US009200259B2

(12) United States Patent
Decaro et al.

(10) Patent No.: US 9,200,259 B2
(45) Date of Patent: Dec. 1, 2015

(54) CANINE CORONAVIRUS VACCINE

(75) Inventors: Nicola Decaro, Bari (IT); Vito Martella, Casamassima (IT); Gabriella Elia, Bari (IT); Canio Buonavoglia, Noicattaro (IT)

(73) Assignees: Nicola Decaro, Bari (IT); Vito Martella, Casamassima (IT); Gabriella Elia, Bari (IT); Canio Buonavoglia, Noicattaro (IT)

( * ) Notice: Subject to any disclaimer, the term of this patent is extended or adjusted under 35 U.S.C. 154(b) by 0 days.

(21) Appl. No.: 14/127,884

(22) PCT Filed: Jun. 26, 2012

(86) PCT No.: PCT/EP2012/062347

§ 371 (c)(1),
(2), (4) Date: Dec. 19, 2013

(87) PCT Pub. No.: WO2013/000905
PCT Pub. Date: Jan. 3, 2013

(65) Prior Publication Data

US 2014/0205621 A1 Jul. 24, 2014

(30) Foreign Application Priority Data

Jun. 28, 2011 (IT) .............................. MI2011A1182

(51) Int. Cl.
| | |
|---|---|
| *A61K 39/215* | (2006.01) |
| *C12N 7/00* | (2006.01) |
| *C07K 14/005* | (2006.01) |
| *A61K 39/12* | (2006.01) |
| *A61K 39/00* | (2006.01) |

(52) U.S. Cl.
CPC . *C12N 7/00* (2013.01); *A61K 39/12* (2013.01); *A61K 39/215* (2013.01); *C07K 14/005* (2013.01); *A61K 39/00* (2013.01); *A61K 2039/525* (2013.01); *A61K 2039/552* (2013.01); *C12N 2770/20021* (2013.01); *C12N 2770/20022* (2013.01); *C12N 2770/20034* (2013.01)

(58) Field of Classification Search
None
See application file for complete search history.

(56) References Cited

FOREIGN PATENT DOCUMENTS

| | | | |
|---|---|---|---|
| EP | 1 780 216 | A1 | 5/2007 |
| WO | WO 93/23421 | A1 | 11/1993 |
| WO | WO 2004/011651 | A1 | 2/2004 |

OTHER PUBLICATIONS

Decaro et al (Veterinary Microbiology 159:239-44, Sep. 14, 2012, Epub Apr. 6, 2012).*
Lorusso et al (Journal of Virology 82:10312-10317, 2008) (in IDS).*

Alessio Lorusso et al., “Gain, Preservation, and Loss of a Group 1a Coronavirus Accessory Glycoprotein”, Journal of Virology, Jul. 30, 2008, vol. 82, No. 20, p. 10312-10317.

Alessio Lorusso et al., “Molecular Characterization of a Canine Respiratory Coronavirus Strain Detected in Italy”, Virus Research, Apr. 1, 2009, vol. 141, No. 1, p. 96-100.

International Search Report, International Application No. PCT/EP2012/062347 mailing date Sep. 20, 2012.

Nicola Decaro et al., “Experimental Infection of Dogs with a Novel Strain of Canine Coronavirus Causing Systemic Disease and Lymphopenia”, Veterinary Microbiology, 2008, vol. 128, No. 3-4, p. 253-260.

Nicola Decaro et al., “Recombinant Canine Coronaviruses in Dogs, Europe”, Emerging Infectious Diseases, Jan. 2010, vol. 16, No. 1, p. 41-47.

Nicola Decaro et al., “Recombinant Canine Coronaviruses Related to Transmissible Gastroenteritis Virus of Swine are Circulating in Dogs”, Journal of Virology, Nov. 26, 2008, vol. 83, No. 3, p. 1532-1537.

* cited by examiner

*Primary Examiner* — Mary E Mosher

(74) *Attorney, Agent, or Firm* — Arent Fox LLP

(57) ABSTRACT

A new pantropic canine coronavirus (CCoV) strain, having reduced pathogenicity, and capable of eliciting an immune response, is described.

4 Claims, 1 Drawing Sheet

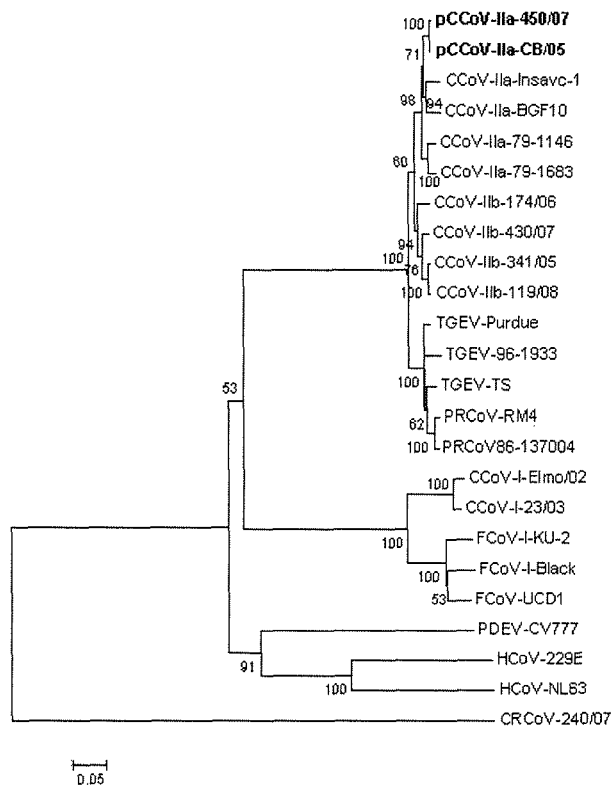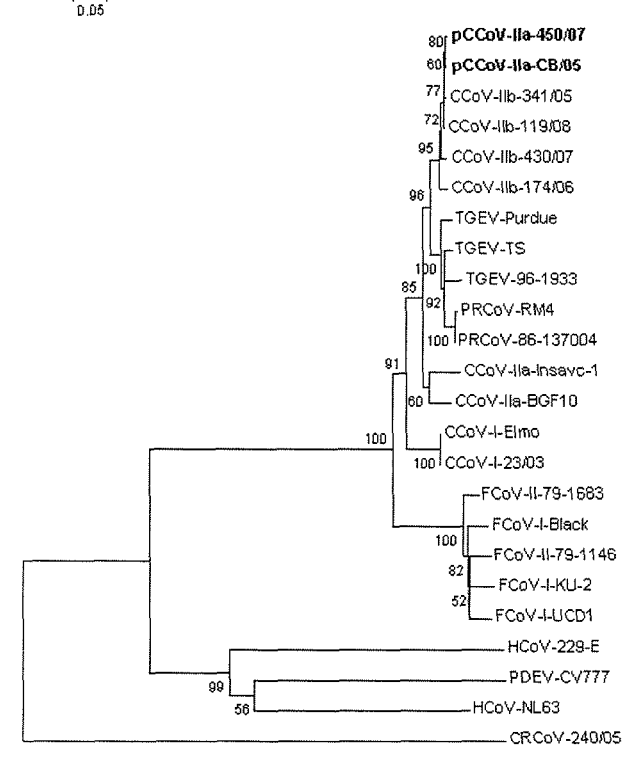

SEQUENCE LISTING

```
<160> NUMBER OF SEQ ID NOS: 16

<210> SEQ ID NO 1
<211> LENGTH: 8618
<212> TYPE: DNA
<213> ORGANISM: Canine coronavirus

<400> SEQUENCE: 1
actaaacttt ggtaatcatt tagttaatgt gccatgattg tgatcttaac ttgcgtctta    60
```

```
ttgttgtgct cgtaccatac tgttgcgagt acgacaaata atgattgtag acaagttaac    120
gtaacacaat tagatggcaa cgaaaatctc attagagact ttttgtttca aaactttaaa    180
gaagaaggaa ctgtagttgt tggtggctat tatcctacag aggtgtggta caactgttct    240
agaacagcaa ctaccactgc ctatgagtat tttaataaca tacatgcatt ttattttgat    300
atggaagcca tggaaaatag cactggtaat gcacgtggta aaccgttatt gtttcatgtt    360
catggtgagc ctgttagtgc tatcatatat atatcggctt ataaaaatga tgtacaacac    420
aggccacttt taaaacatgg gttagtgtgc ataactaaaa ctcgcaatat tgactataac    480
agcttcacta gcagccagtg gaattccata tgtacaggta atgacagaaa aattcctttc    540
tctgtcatac ccacggacaa tggaacaaaa atctatggac ttgagtggaa tgacgaattt    600
gttacagcct atattagtgg tcattcttat aattggaaca tcaataataa ttggtttaac    660
aatgttacac tactttattc ccgctcaagt actgctacat ggcaacacag tgctgcatat    720
gtttaccaag gtgttttctaa cttcacttat tacaagttaa ataacaccaa tggtttaaaa    780
acttatgaat tttgtgatga ttatgaatat tgcactggct acgctactaa tgtctttgct    840
cccactgtag gaggttacat acctgatgga tttagttttta acaattggtt tttgcttaca    900
aatggctcca cttttgttag tggcagattt gtaacaaatc aaccattatt agttaattgt    960
ttatggccag tgcccagttt tggtgtggca gcacaagaat tttgttttga aggtgcgcag   1020
tttagtcagt gcaatggtgt gtcttttaaat aacacagtgg atgttattag attcaatctt   1080
aattttaccg cagatgtaca atctggcatg ggtgctacag tgttctcatt gaatacaaca   1140
ggtggtgtca ttcttgaaat tttatgttat aatgacacag tgagtgagtc tagtttttac   1200
agttatggtg aaattccatt tggcataact gatggaccac ggtactgtta tgtactttac   1260
aatggcacag ctcttaagta tttaggaaca ttaccaccta gtgtaaagga aattgctatt   1320
agtaagtggg gccattttta tattaatggt tacaatttct ttagcacatt tcctattgat   1380
tgtatatctt ttaatttaac cactggtact agtggagctt tttggactat tgcttacaca   1440
tcgtacactg aagcattagt acaagttgaa aacacagcta ttaaaaaggt gacgtattgt   1500
aacagtcaca ttaataacat taaatgttct caacttactg ctaatttgca aaatggtttt   1560
tatcctgttg cttcaagtga agttggtctt gtcaataaga gtgttgtgtt actacctagt   1620
ttctattcac ataccagtgt aatataact attgatcttg gtatgaagcg tagtggttat   1680
ggtcaaccta tagcctcagc attaagtaac atcacactac cgatgcagga taataacacc   1740
gatgtgtatt gcattcgttc taatcaattt tcagtttacg tgcattccac ttgtaaaagt   1800
tctttatggg acaatgtgtt taattctgac tgcacagatt ttttacatgc tatagctgtt   1860
ataaaaactg gtacttgtcc tttctcattt gataaattga caattaccct aactttttaac   1920
aagttctgtt tttcattgaa tcctgttggt gccaattgca aatttgatgt tgctgcccgt   1980
acaagaacca atgagcaggt tgttagaagt ttatatgtga tatatgaaga aggagacaat   2040
atagtgggtg taccgtctga taatagtggt ctgcacgatt tgtcagtgtt acacttagac   2100
tcctgtacag attacaatat atatggtaga actggtgttg gtattattag acaaactaac   2160
agcacactac ttagtggctt atattacaca tcactatcag gtgatttgtt aggttttaaa   2220
aatgtcactg acggtgttgt ctattctgta acaccatgtg atgtaagtgc acaagctgct   2280
gttattgatg gtgccatagt tggagctatg acttccatta atagtgaact gttaggtcta   2340
actcattgga caacaacacc taattttttat tattactcca tatataatta tacaaatgcg   2400
```

-continued

```
agaactcgtg gcactgcaat cgacagtaac gatgttgatt gtgaacctat cataacctat    2460
tctaatatag gtgtttgtaa aaatggagct ttggttttta ttaacgtcac acattctgat    2520
ggtgacgttc aaccaattag caccggtaat gtcacgatac ctacaaattt tactatatct    2580
gtgcaagtcg aatatattca ggtttacact acaccagtgt caatagactg ttcaagatac    2640
gtctgcaatg gtaatcctag atgcaataaa ttgttaacac aatatgtctc tgcatgtcaa    2700
actattgagc aagcacttgc aatgggtgcc agacttgaaa acatggaagt tgattccatg    2760
ttgtttgttt ctgaaaatgc ccttaaattg gcatctgttg aagcattcaa tagtacggaa    2820
actctagatc ctatttacaa agaatggcct aacattggtg gttcttggct aggaggttta    2880
aaagacatat tgccatctca caatagcaaa cgtaagtacc ggtctgctat agaagatttg    2940 cttttttgata aggttgtgac atctggctta ggtacagtcg atgaagatta caaacgttgt    3000
acgggtggct atgacatagc tgacttagtg tgtgcacaat attacaatgg catcatggtg    3060
ttacctggtg tggctaatga tgacaagatg gctatgtaca ctgcatctct tgcaggtggt    3120
ataacattag gtgcacttgg tggtggtgca gtgtctatac cttttgcagt agcagttcag    3180
gctagactta attatgtagc tttacaaact gacgtattga acaaaaacca gcagattctg    3240
gctaatgctt tcaatcaagc gattggtaac attacacagg catttggtaa ggttaatgat    3300
gctatacatc aaacgtcaaa aggtcttgct actgttgcta aagcattggc aaaagtgcaa    3360
gatgttgtta acacacaagg gcaagcttta agccacctaa cagtacaatt gcaaaataat    3420
tttcaagcca ttagtagttc cattagtgac atttataaca ggcttgatga gttgagtgcg    3480
gatgcacaag ttgacaggct gattacagga cgacttacag cacttaatgc atttgtgtct    3540
cagactttaa ccagacaagc agaggttagg gctagtagac aacttgctaa agacaaagtt    3600
aatgaatgcg ttaggtctca atcccaaaga tttggattct gtggtaatgg tacacatttg    3660
ttttcacttg caaatgcagc accaaatggc atgattttct ttcacacagt gctattacca    3720
acagcttatg aaactgtgac ggcctggtca ggtatttgtg catcagatgg cgatcgcact    3780
tttggacttg ttgttaaaga tgtccagctg acgctatttc gcaatttaga tgacaaattc    3840
tatttgacac ctagaactat gtatcagcct agagttgcaa ctagttctga ttttgttcaa    3900
attgaagggt gtgatgtctt gtttgtcaat gcaactgtaa ttgagttgcc tagtattata    3960
cctgattata tcgatattaa tcagactgtt caagacatat tagaaaatta cagaccaaat    4020
tggacagtac ctgaattaac acttgacatt ttcaacgcaa cctacttaaa cctgactggt    4080
gaaattaatg acttagaatt caggtcagaa aagctacata acaccacggt agaacttgct    4140
gttctcattg acaatattaa caatacatta gtcaatcttg aatggctcaa tagaattgaa    4200
acttatgtaa aatggcccttg gtatgtatgg ctactaatag gcttagtagt aatatttttgc    4260 ataccattac tgctattttg ctgttgtagt acaggttgct gtgggtgcat aggttgctta    4320
ggaagttgtt gtcactctat ttgtagtaga agacaatttg aaaattatga accaattgag    4380
aaagtgcatg tccattaaat tcaaaataaa tctcttaaga actaaactta tgagtcatta    4440
caggtcttgt atggacattg tcaaatctat tgacacatcc gtagacgctg tacttgacga    4500
acttgatcgt gcatactttg ctgtaactct aaagtagag tttaagactg gtaaactact    4560
tgtgtgtata ggttttggtg atacacctct tgaggctaag gataaagcat atgctaaact    4620
tggtttctct attattgaag aagtcaatag tcatacagtt gtttgatatt accttttgaa    4680
actagacttc ttatcatcga acaaacaaaa cctaaagcat taagtgctac aaaacaatca    4740
aagagagatt atagaaaaat tgccattcta aattccatga gaaaatgatt ggtggacttt    4800
```

```
ttcttatttc tagctttgta ccgtagtaca aactttaaga cgtgtgtcgg tatcttaatg    4860
tttaagattg tatcaatgac acttataggg cctatgctta tagcatatgg ttactacatt    4920
gatggcattg ttacaacaac tgtcttagct ttaagatttg tctacttatc atacttttgg    4980
tatgttaata gtaggtttga attcatctta tacaatacaa cgacactcat gtttgtacat    5040
ggcagagctg caccgtttat gagaagttct cacagctcta tttatgtcac attgtacggt    5100
ggcataaatt atatgtttgt gaatgacctc acgttgcatt ttgtagaccc tatgcttgta    5160
agcatagcaa tacgtggctt agctcatgct gatctaactg ttgttagagc agttgaactt    5220
ctcaatggtg attttatcta tgtattttca caggagcccg tagtcggtgt ttacaatgca    5280
gccttttctc aggcggttct aaacgaaatt gacttaaaag aagaagaaga agaccatacc    5340
tatgacgttc cctagggcat tgactgtcat agatgacaat ggaatggtca ttagtatcat    5400
tttctggttc ctgttgataa ttatattgat attactttca atagcattgc taaatataat    5460
taagctatgc atggtatgtt gtaacttagg aagaacagtt attattgttc cagcgcaaca    5520
tgcctatgat gcctataaga attttatgcg aattaaagca tataaccccg acgaagcact    5580
ccttgtttga actaaacaaa atgaagattt tgttagtatt agcgtgtgca attgcatgcg    5640
catgtggtga acgttattgc gctatgaaat ctgactcaga tacttcgtgt cgcaatggta    5700
ccactactga ttgcgaatca tgcttcaacg gaggtgatct tatttggcat cttgcaaact    5760
ggaacttcag ctggtctgta atattgatcg tttttataac ggttttacaa tatggtagac    5820
ctcaatttag ctggttcgtg tatggcatta aaatgcttat tatgtggcta ctatggccca    5880
ttgttctggc tcttacgatt tttaatgcat actcggaata cgaagcttcc agatatgtaa    5940
tgttcggctt tagtgttgca ggtgcaattg ttacatttat actttggatt atgtatttg    6000 ttagatccat tcagttatac agaaggacta agtcttggtg gtctttcaac cctgaaacta    6060
acgcaattct ttgcgttagt gcattaggaa ggagctatgt gcttcctctt gaaggtgtgc    6120
caactggtgt cactttaaca ttgctctcag ggaatttgta cgctgaaggg ttcaaaattg    6180
caggtggtat gaacatcgac aatttgccaa agtacgtaat ggttgcatta cctagcagga    6240
ccattgtcta cacacttgtt ggtaagaaat tgaaagcaag tagtgcaaca ggatgggctt    6300
actatgtaaa atctaaagct ggtgattact caacagatgc acgaactgac aatttgagtg    6360
agcaagaaaa attattacat atggtataac taaacttcta aatgaccaac cagggacaac    6420
gcgttagctg gggagatgaa tctaccaaaa agcgtggtcg ttccaattct cgtggccgga    6480
agaataatac tatacctctt tcattcttca accccattac cctccaacaa ggttcaaaat    6540
tttggaactt atgtccgaga actttgtac ccaaaggaat aggtaacaag gatcaacaga    6600
ttggttattg gaatagacaa actcgctatc gcatggtgaa gggtcagcgt aaagagcttc    6660
ctgaaaggtg gttcttctac tatttaggta ctggtcctca cgccgatgct aaatttaaag    6720
atagaataga tggagttgtc tgggttgcca aggatggtgc catgaataag ccaaccacac    6780
ttggtaatcg tggtgctaat aatgaatcca aagctttgaa attcgatggt aaagtaccag    6840
tagaatttca acttgaagtg aaccaatcaa gggacaattc aaggtcacgc tctcaatcta    6900
gatcccagtc tagaaataga tctcaatcta gaggaaggca acaatccaat aacaagaagg    6960
atgacagtgt agaacaagct gttcttgctg cactcaaaaa gttaggtgtt gacacagaaa    7020
aacaacaaca acgctctcgt tctaaatcca aggaacgtag caactctaag acaagagaca    7080
ctacacctaa gaatgaaaac aaacacacct ggaagagaac tgcaggtaaa ggtgatgtga    7140
```

```
caaaatttta tggagctaga agtagttcag ccaattttgg tgacagcgat ctcgttgcca    7200
atggtagcgg tgccaagcat tacccacaac tggctgaatg tgttccatct gtatctagca    7260
ttctgtttgg aagctattgg actgcaaagg aagatggcga ccagattgaa gtcacattca    7320
cacataaata ccacttgcca aaagatgatc ctaagactgg acaattcctt cagcagatta    7380
atgcctatgc tcgtccatca gaggtggcaa agaacagag acaacgcaaa gctcgttcta    7440
aatctgcaga aggtcagag caagaggttg tacctgatgc attaacagaa aattacacag    7500
atgtgtttga tgacacacag gttgagatta ttgatgaggt aacgaactaa acgaatgctc    7560
gttttcctcc atgctgtatt tatcacagtt ttaatcttac tactaattgg tagactccaa    7620
ttattagaaa gattattact taatcattcc ctcaatctta aaactgtcaa taatgtttta    7680
ggtgtgactg acactggtct gaaagtaaat tgcttacagc ttttgaaacc agactgtctt    7740
gattttaaca tcttacatag gagtttggca gaaaccagat tactaaaagt agtacttcga    7800
gtaatctttc tagtattact agggttttgc tgctacagat tgttagtcac attaatttag    7860
catcatgaag ttttttgattt ttgtactgtg tctttctctt gtgaatggat atggaattag    7920
aagaagcata caagaacatg acccaaaaga gtcccatgaa caccccgacca tgacatggga    7980 attattggaa agatttgttg gaagtacctt gtacatcaca acaaaccaaa tcctatctct    8040
accaactgga gcgcaaattt attgtgatga gattgaagga ttccaatgct cttggcctgg    8100
ttataaagct tatgctcatg atcacattga ttatcatttt gatctttcca acccgttcta    8160
ttcttttgta aatacattct acatttcttt aggtgataga aagaaaaaa tttatcttag    8220 agtggttggt gcaacaccaa aagagaaaag attgaatgtt ggttgtagaa catctttctc    8280
agttaacatg ccaattggaa ctcagattta ccatgacaaa gatatgcaat atcttgtcga    8340
gggaagacat cttgagtgtg ctcacagagt ttactttgtg aagtactgtc caaaccatgc    8400
acatggttac tgctttaatg acaggctaaa ggtttataat cttggtcgtg tcaaaagcag    8460
aaaggctttt gagaaaatca accaacatca gaaaagtgag ttgtaaggca acccgatgtt    8520
taaaactggt ttttccgagg aattactggt catcgcgctg tctactcttg tacagaatgg    8580
taagcacgtg taataggagg tacaagcaac cctattgc                           8618
```

<210> SEQ ID NO 2
<211> LENGTH: 1454
<212> TYPE: PRT
<213> ORGANISM: Canine coronavirus

<400> SEQUENCE: 2

```
Met Ile Val Ile Leu Thr Cys Val Leu Leu Cys Ser Tyr His Thr
1               5                   10                  15

Val Ala Ser Thr Thr Asn Asn Asp Cys Arg Gln Val Asn Val Thr Gln
            20                  25                  30

Leu Asp Gly Asn Glu Asn Leu Ile Arg Asp Phe Leu Phe Gln Asn Phe
        35                  40                  45

Lys Glu Glu Gly Thr Val Val Val Gly Gly Tyr Tyr Pro Thr Glu Val
    50                  55                  60

Trp Tyr Asn Cys Ser Arg Thr Ala Thr Thr Ala Tyr Glu Tyr Phe
65                  70                  75                  80

Asn Asn Ile His Ala Phe Tyr Phe Asp Met Glu Ala Met Glu Asn Ser
                85                  90                  95

Thr Gly Asn Ala Arg Gly Lys Pro Leu Leu Phe His Val His Gly Glu
            100                 105                 110
```

-continued

```
Pro Val Ser Ala Ile Ile Tyr Ile Ser Ala Tyr Lys Asn Asp Val Gln
            115                 120                 125

His Arg Pro Leu Leu Lys His Gly Leu Val Cys Ile Thr Lys Thr Arg
130                 135                 140

Asn Ile Asp Tyr Asn Ser Phe Thr Ser Gln Trp Asn Ser Ile Cys
145                 150                 155                 160

Thr Gly Asn Asp Arg Lys Ile Pro Phe Ser Val Ile Pro Thr Asp Asn
                165                 170                 175

Gly Thr Lys Ile Tyr Gly Leu Glu Trp Asn Asp Glu Phe Val Thr Ala
            180                 185                 190

Tyr Ile Ser Gly His Ser Tyr Asn Trp Asn Ile Asn Asn Asn Trp Phe
            195                 200                 205

Asn Asn Val Thr Leu Leu Tyr Ser Arg Ser Ser Thr Ala Thr Trp Gln
210                 215                 220

His Ser Ala Ala Tyr Val Tyr Gln Gly Val Ser Asn Phe Thr Tyr Tyr
225                 230                 235                 240

Lys Leu Asn Asn Thr Asn Gly Leu Lys Thr Tyr Glu Phe Cys Asp Asp
                245                 250                 255

Tyr Glu Tyr Cys Thr Gly Tyr Ala Thr Asn Val Phe Ala Pro Thr Val
            260                 265                 270

Gly Gly Tyr Ile Pro Asp Gly Phe Ser Phe Asn Asn Trp Phe Leu Leu
            275                 280                 285

Thr Asn Gly Ser Thr Phe Val Ser Gly Arg Phe Val Thr Asn Gln Pro
            290                 295                 300

Leu Leu Val Asn Cys Leu Trp Pro Val Pro Ser Phe Gly Val Ala Ala
305                 310                 315                 320

Gln Glu Phe Cys Phe Glu Gly Ala Gln Phe Ser Gln Cys Asn Gly Val
                325                 330                 335

Ser Leu Asn Asn Thr Val Asp Val Ile Arg Phe Asn Leu Asn Phe Thr
            340                 345                 350

Ala Asp Val Gln Ser Gly Met Gly Ala Thr Val Phe Ser Leu Asn Thr
            355                 360                 365

Thr Gly Gly Val Ile Leu Glu Ile Leu Cys Tyr Asn Asp Thr Val Ser
370                 375                 380

Glu Ser Ser Phe Tyr Ser Tyr Gly Glu Ile Pro Phe Gly Ile Thr Asp
385                 390                 395                 400

Gly Pro Arg Tyr Cys Tyr Val Leu Tyr Asn Gly Thr Ala Leu Lys Tyr
                405                 410                 415

Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
            435                 440                 445

Asp Cys Ile Ser Phe Asn Leu Thr Thr Gly Thr Ser Gly Ala Phe Trp
450                 455                 460

Thr Ile Ala Tyr Thr Ser Tyr Thr Glu Ala Leu Val Gln Val Glu Asn
465                 470                 475                 480

Thr Ala Ile Lys Lys Val Thr Tyr Cys Asn Ser His Ile Asn Asn Ile
                485                 490                 495

Lys Cys Ser Gln Leu Thr Ala Asn Leu Gln Asn Gly Phe Tyr Pro Val
            500                 505                 510

Ala Ser Ser Glu Val Gly Leu Val Asn Lys Ser Val Val Leu Leu Pro
            515                 520                 525

Ser Phe Tyr Ser His Thr Ser Val Asn Ile Thr Ile Asp Leu Gly Met
```

```
                530             535             540
Lys Arg Ser Gly Tyr Gly Gln Pro Ile Ala Ser Ala Leu Ser Asn Ile
545                 550             555                 560

Thr Leu Pro Met Gln Asp Asn Thr Asp Val Tyr Cys Ile Arg Ser
                565             570             575

Asn Gln Phe Ser Val Tyr Val His Ser Thr Cys Lys Ser Ser Leu Trp
            580             585             590

Asp Asn Val Phe Asn Ser Asp Cys Thr Asp Phe Leu His Ala Ile Ala
        595             600             605

Val Ile Lys Thr Gly Thr Cys Pro Phe Ser Phe Asp Lys Leu Asn Asn
        610             615             620

Tyr Leu Thr Phe Asn Lys Phe Cys Phe Ser Leu Asn Pro Val Gly Ala
625             630             635                 640

Asn Cys Lys Phe Asp Val Ala Ala Arg Thr Arg Thr Asn Glu Gln Val
            645             650             655

Val Arg Ser Leu Tyr Val Ile Tyr Glu Glu Gly Asp Asn Ile Val Gly
            660             665             670

Val Pro Ser Asp Asn Ser Gly Leu His Asp Leu Ser Val Leu His Leu
        675             680             685

Asp Ser Cys Thr Asp Tyr Asn Ile Tyr Gly Arg Thr Gly Val Gly Ile
        690             695             700

Ile Arg Gln Thr Asn Ser Thr Leu Leu Ser Gly Leu Tyr Tyr Thr Ser
705             710             715                 720

Leu Ser Gly Asp Leu Leu Gly Phe Lys Asn Val Thr Asp Gly Val Val
                725             730             735

Tyr Ser Val Thr Pro Cys Asp Val Ser Ala Gln Ala Ala Val Ile Asp
            740             745             750

Gly Ala Ile Val Gly Ala Met Thr Ser Ile Asn Ser Glu Leu Leu Gly
            755             760             765

Leu Thr His Trp Thr Thr Thr Pro Asn Phe Tyr Tyr Tyr Ser Ile Tyr
770             775             780

Asn Tyr Thr Asn Ala Arg Thr Arg Gly Thr Ala Ile Asp Ser Asn Asp
785             790             795                 800

Val Asp Cys Glu Pro Ile Ile Thr Tyr Ser Asn Ile Gly Val Cys Lys
            805             810             815

Asn Gly Ala Leu Val Phe Ile Asn Val Thr His Ser Asp Gly Asp Val
            820             825             830

Gln Pro Ile Ser Thr Gly Asn Val Thr Ile Pro Thr Asn Phe Thr Ile
        835             840             845

Ser Val Gln Val Glu Tyr Ile Gln Val Tyr Thr Thr Pro Val Ser Ile
850             855             860

Asp Cys Ser Arg Tyr Val Cys Asn Gly Asn Pro Arg Cys Asn Lys Leu
865             870             875                 880

Leu Thr Gln Tyr Val Ser Ala Cys Gln Thr Ile Glu Gln Ala Leu Ala
            885             890             895

Met Gly Ala Arg Leu Glu Asn Met Glu Val Asp Ser Met Leu Phe Val
            900             905             910

Ser Glu Asn Ala Leu Lys Leu Ala Ser Val Glu Ala Phe Asn Ser Thr
            915             920             925

Glu Thr Leu Asp Pro Ile Tyr Lys Glu Trp Pro Asn Ile Gly Gly Ser
        930             935             940

Trp Leu Gly Gly Leu Lys Asp Ile Leu Pro Ser His Asn Ser Lys Arg
945             950             955                 960
```

```
Lys Tyr Arg Ser Ala Ile Glu Asp Leu Leu Phe Asp Lys Val Val Thr
                965                 970                 975

Ser Gly Leu Gly Thr Val Asp Glu Asp Tyr Lys Arg Cys Thr Gly Gly
            980                 985                 990

Tyr Asp Ile Ala Asp Leu Val Cys Ala Gln Tyr Tyr Asn Gly Ile Met
        995                 1000                1005

Val Leu Pro Gly Val Ala Asn Asp Asp Lys Met Ala Met Tyr Thr
    1010                1015                1020

Ala Ser Leu Ala Gly Gly Ile Thr Leu Gly Ala Leu Gly Gly Gly
    1025                1030                1035

Ala Val Ser Ile Pro Phe Ala Val Ala Val Gln Ala Arg Leu Asn
    1040                1045                1050

Tyr Val Ala Leu Gln Thr Asp Val Leu Asn Lys Asn Gln Gln Ile
    1055                1060                1065

Leu Ala Asn Ala Phe Asn Gln Ala Ile Gly Asn Ile Thr Gln Ala
    1070                1075                1080

Phe Gly Lys Val Asn Asp Ala Ile His Gln Thr Ser Lys Gly Leu
    1085                1090                1095

Ala Thr Val Ala Lys Ala Leu Ala Lys Val Gln Asp Val Val Asn
    1100                1105                1110

Thr Gln Gly Gln Ala Leu Ser His Leu Thr Val Gln Leu Gln Asn
    1115                1120                1125

Asn Phe Gln Ala Ile Ser Ser Ser Ile Ser Asp Ile Tyr Asn Arg
    1130                1135                1140

Leu Asp Glu Leu Ser Ala Asp Ala Gln Val Asp Arg Leu Ile Thr
    1145                1150                1155

Gly Arg Leu Thr Ala Leu Asn Ala Phe Val Ser Gln Thr Leu Thr
    1160                1165                1170

Arg Gln Ala Glu Val Arg Ala Ser Arg Gln Leu Ala Lys Asp Lys
    1175                1180                1185

Val Asn Glu Cys Val Arg Ser Gln Ser Gln Arg Phe Gly Phe Cys
    1190                1195                1200

Gly Asn Gly Thr His Leu Phe Ser Leu Ala Asn Ala Ala Pro Asn
    1205                1210                1215

Gly Met Ile Phe Phe His Thr Val Leu Leu Pro Thr Ala Tyr Glu
    1220                1225                1230

Thr Val Thr Ala Trp Ser Gly Ile Cys Ala Ser Asp Gly Asp Arg
    1235                1240                1245

Thr Phe Gly Leu Val Val Lys Asp Val Gln Leu Thr Leu Phe Arg
    1250                1255                1260

Asn Leu Asp Asp Lys Phe Tyr Leu Thr Pro Arg Thr Met Tyr Gln
    1265                1270                1275

Pro Arg Val Ala Thr Ser Ser Asp Phe Val Gln Ile Glu Gly Cys
    1280                1285                1290

Asp Val Leu Phe Val Asn Ala Thr Val Ile Glu Leu Pro Ser Ile
    1295                1300                1305

Ile Pro Asp Tyr Ile Asp Ile Asn Gln Thr Val Gln Asp Ile Leu
    1310                1315                1320

Glu Asn Tyr Arg Pro Asn Trp Thr Val Pro Glu Leu Thr Leu Asp
    1325                1330                1335

Ile Phe Asn Ala Thr Tyr Leu Asn Leu Thr Gly Glu Ile Asn Asp
    1340                1345                1350
```

```
Leu Glu  Phe Arg Ser Glu  Lys Leu His Asn Thr  Thr Val Glu Leu
    1355              1360                 1365

Ala Val  Leu Ile Asp Asn  Ile Asn Asn Thr  Leu Val Asn Leu Glu
    1370              1375                 1380

Trp Leu  Asn Arg Ile Glu  Thr Tyr Val Lys  Trp Pro Trp Tyr Val
    1385              1390                 1395

Trp Leu  Leu Ile Gly Leu  Val Val Ile Phe  Cys Ile Pro Leu Leu
    1400              1405                 1410

Leu Phe  Cys Cys Cys Ser  Thr Gly Cys Cys  Gly Cys Ile Gly Cys
    1415              1420                 1425

Leu Gly  Ser Cys Cys His  Ser Ile Cys Ser  Arg Arg Gln Phe Glu
    1430              1435                 1440

Asn Tyr  Glu Pro Ile Glu  Lys Val His Val  His
    1445              1450

<210> SEQ ID NO 3
<211> LENGTH: 71
<212> TYPE: PRT
<213> ORGANISM: Canine coronavirus

<400> SEQUENCE: 3

Met Asp Ile Val Lys Ser Ile Asp Thr Ser Val Asp Ala Val Leu Asp
1               5                   10                  15

Glu Leu Asp Arg Ala Tyr Phe Ala Val Thr Leu Lys Val Glu Phe Lys
            20                  25                  30

Thr Gly Lys Leu Leu Val Cys Ile Gly Phe Gly Asp Thr Pro Leu Glu
        35                  40                  45

Ala Lys Asp Lys Ala Tyr Ala Lys Leu Gly Phe Ser Ile Ile Glu Glu
    50                  55                  60

Val Asn Ser His Thr Val Val
65                  70

<210> SEQ ID NO 4
<211> LENGTH: 22
<212> TYPE: PRT
<213> ORGANISM: Canine coronavirus

<400> SEQUENCE: 4

Met Leu Asn Leu Val Ser Leu Leu Leu Lys Lys Ser Ile Val Ile Gln
1               5                   10                  15

Leu Phe Asp Ile Thr Phe
            20

<210> SEQ ID NO 5
<211> LENGTH: 13
<212> TYPE: PRT
<213> ORGANISM: Canine coronavirus

<400> SEQUENCE: 5

Met Ile Gly Gly Leu Phe Leu Ile Ser Ser Phe Val Pro
1               5                   10

<210> SEQ ID NO 6
<211> LENGTH: 82
<212> TYPE: PRT
<213> ORGANISM: Canine coronavirus

<400> SEQUENCE: 6

Met Thr Phe Pro Arg Ala Leu Thr Val Ile Asp Asp Asn Gly Met Val
1               5                   10                  15
```

Ile Ser Ile Ile Phe Trp Phe Leu Leu Ile Ile Leu Ile Leu Leu
                20                  25                  30

Ser Ile Ala Leu Leu Asn Ile Ile Lys Leu Cys Met Val Cys Cys Asn
         35                  40                  45

Leu Gly Arg Thr Val Ile Ile Val Pro Ala Gln His Ala Tyr Asp Ala
50                  55                  60

Tyr Lys Asn Phe Met Arg Ile Lys Ala Tyr Asn Pro Asp Glu Ala Leu
65                  70                  75                  80

Leu Val

<210> SEQ ID NO 7
<211> LENGTH: 262
<212> TYPE: PRT
<213> ORGANISM: Canine coronavirus

<400> SEQUENCE: 7

Met Lys Ile Leu Leu Val Leu Ala Cys Ala Ile Ala Cys Ala Cys Gly
1               5                   10                  15

Glu Arg Tyr Cys Ala Met Lys Ser Asp Ser Asp Thr Ser Cys Arg Asn
                20                  25                  30

Gly Thr Thr Thr Asp Cys Glu Ser Cys Phe Asn Gly Gly Asp Leu Ile
            35                  40                  45

Trp His Leu Ala Asn Trp Asn Phe Ser Trp Ser Val Ile Leu Ile Val
        50                  55                  60

Phe Ile Thr Val Leu Gln Tyr Gly Arg Pro Gln Phe Ser Trp Phe Val
65                  70                  75                  80

Tyr Gly Ile Lys Met Leu Ile Met Trp Leu Leu Trp Pro Ile Val Leu
                85                  90                  95

Ala Leu Thr Ile Phe Asn Ala Tyr Ser Glu Tyr Glu Ala Ser Arg Tyr
                100                 105                 110

Val Met Phe Gly Phe Ser Val Ala Gly Ala Ile Val Thr Phe Ile Leu
            115                 120                 125

Trp Ile Met Tyr Phe Val Arg Ser Ile Gln Leu Tyr Arg Arg Thr Lys
        130                 135                 140

Ser Trp Trp Ser Phe Asn Pro Glu Thr Asn Ala Ile Leu Cys Val Ser
145                 150                 155                 160

Ala Leu Gly Arg Ser Tyr Val Leu Pro Leu Glu Gly Val Pro Thr Gly
                165                 170                 175

Val Thr Leu Thr Leu Leu Ser Gly Asn Leu Tyr Ala Glu Gly Phe Lys
            180                 185                 190

Ile Ala Gly Gly Met Asn Ile Asp Asn Leu Pro Lys Tyr Val Met Val
        195                 200                 205

Ala Leu Pro Ser Arg Thr Ile Val Tyr Thr Leu Val Gly Lys Lys Leu
    210                 215                 220

Lys Ala Ser Ser Ala Thr Gly Trp Ala Tyr Tyr Val Lys Ser Lys Ala
225                 230                 235                 240

Gly Asp Tyr Ser Thr Asp Ala Arg Thr Asp Asn Leu Ser Glu Gln Glu
                245                 250                 255

Lys Leu Leu His Met Val
            260

<210> SEQ ID NO 8
<211> LENGTH: 382
<212> TYPE: PRT
<213> ORGANISM: Canine coronavirus

<400> SEQUENCE: 8

```
Met Thr Asn Gln Gly Gln Arg Val Ser Trp Gly Asp Glu Ser Thr Lys
1               5                   10                  15

Lys Arg Gly Arg Ser Asn Ser Arg Gly Arg Lys Asn Asn Thr Ile Pro
            20                  25                  30

Leu Ser Phe Phe Asn Pro Ile Thr Leu Gln Gln Gly Ser Lys Phe Trp
        35                  40                  45

Asn Leu Cys Pro Arg Asp Phe Val Pro Lys Gly Ile Gly Asn Lys Asp
    50                  55                  60

Gln Gln Ile Gly Tyr Trp Asn Arg Gln Thr Arg Tyr Arg Met Val Lys
65                  70                  75                  80

Gly Gln Arg Lys Glu Leu Pro Glu Arg Trp Phe Phe Tyr Tyr Leu Gly
                85                  90                  95

Thr Gly Pro His Ala Asp Ala Lys Phe Lys Asp Arg Ile Asp Gly Val
            100                 105                 110

Val Trp Val Ala Lys Asp Gly Ala Met Asn Lys Pro Thr Thr Leu Gly
        115                 120                 125

Asn Arg Gly Ala Asn Asn Glu Ser Lys Ala Leu Lys Phe Asp Gly Lys
    130                 135                 140

Val Pro Val Glu Phe Gln Leu Glu Val Asn Gln Ser Arg Asp Asn Ser
145                 150                 155                 160

Arg Ser Arg Ser Gln Ser Arg Ser Gln Ser Arg Asn Arg Ser Gln Ser
                165                 170                 175

Arg Gly Arg Gln Gln Ser Asn Asn Lys Lys Asp Asp Ser Val Glu Gln
            180                 185                 190

Ala Val Leu Ala Ala Leu Lys Lys Leu Gly Val Asp Thr Glu Lys Gln
        195                 200                 205

Gln Gln Arg Ser Arg Ser Lys Ser Lys Glu Arg Ser Asn Ser Lys Thr
    210                 215                 220

Arg Asp Thr Thr Pro Lys Asn Glu Asn Lys His Thr Trp Lys Arg Thr
225                 230                 235                 240

Ala Gly Lys Gly Asp Val Thr Lys Phe Tyr Gly Ala Arg Ser Ser Ser
                245                 250                 255

Ala Asn Phe Gly Asp Ser Asp Leu Val Ala Asn Gly Ser Gly Ala Lys
            260                 265                 270

His Tyr Pro Gln Leu Ala Glu Cys Val Pro Ser Val Ser Ser Ile Leu
        275                 280                 285

Phe Gly Ser Tyr Trp Thr Ala Lys Glu Asp Gly Asp Gln Ile Glu Val
    290                 295                 300

Thr Phe Thr His Lys Tyr His Leu Pro Lys Asp Asp Pro Lys Thr Gly
305                 310                 315                 320

Gln Phe Leu Gln Gln Ile Asn Ala Tyr Ala Arg Pro Ser Glu Val Ala
                325                 330                 335

Lys Glu Gln Arg Gln Arg Lys Ala Arg Ser Lys Ser Ala Glu Arg Ser
            340                 345                 350

Glu Gln Glu Val Val Pro Asp Ala Leu Thr Glu Asn Tyr Thr Asp Val
        355                 360                 365

Phe Asp Asp Thr Gln Val Glu Ile Ile Asp Glu Val Thr Asn
    370                 375                 380
```

<210> SEQ ID NO 9
<211> LENGTH: 101
<212> TYPE: PRT

<213> ORGANISM: Canine coronavirus

<400> SEQUENCE: 9

Met Leu Val Phe Leu His Ala Val Phe Ile Thr Val Leu Ile Leu Leu
1               5                   10                  15

Leu Ile Gly Arg Leu Gln Leu Leu Glu Arg Leu Leu Leu Asn His Ser
            20                  25                  30

Leu Asn Leu Lys Thr Val Asn Asn Val Leu Gly Val Thr Asp Thr Gly
        35                  40                  45

Leu Lys Val Asn Cys Leu Gln Leu Leu Lys Pro Asp Cys Leu Asp Phe
    50                  55                  60

Asn Ile Leu His Arg Ser Leu Ala Glu Thr Arg Leu Leu Lys Val Val
65                  70                  75                  80

Leu Arg Val Ile Phe Leu Val Leu Leu Gly Phe Cys Cys Tyr Arg Leu
                85                  90                  95

Leu Val Thr Leu Ile
            100

<210> SEQ ID NO 10
<211> LENGTH: 213
<212> TYPE: PRT
<213> ORGANISM: Canine coronavirus

<400> SEQUENCE: 10

Met Lys Phe Leu Ile Phe Val Leu Cys Leu Ser Leu Val Asn Gly Tyr
1               5                   10                  15

Gly Ile Arg Arg Ser Ile Gln Glu His Asp Pro Lys Glu Ser His Glu
            20                  25                  30

His Pro Thr Met Thr Trp Glu Leu Leu Glu Arg Phe Val Gly Ser Thr
        35                  40                  45

Leu Tyr Ile Thr Thr Asn Gln Ile Leu Ser Leu Pro Thr Gly Ala Gln
    50                  55                  60

Ile Tyr Cys Asp Glu Ile Glu Gly Phe Gln Cys Ser Trp Pro Gly Tyr
65                  70                  75                  80

Lys Ala Tyr Ala His Asp His Ile Asp Tyr His Phe Asp Leu Ser Asn
                85                  90                  95

Pro Phe Tyr Ser Phe Val Asn Thr Phe Tyr Ile Ser Leu Gly Asp Arg
            100                 105                 110

Lys Glu Lys Ile Tyr Leu Arg Val Val Gly Ala Thr Pro Lys Glu Lys
        115                 120                 125

Arg Leu Asn Val Gly Cys Arg Thr Ser Phe Ser Val Asn Met Pro Ile
    130                 135                 140

Gly Thr Gln Ile Tyr His Asp Lys Asp Met Gln Tyr Leu Val Glu Gly
145                 150                 155                 160

Arg His Leu Glu Cys Ala His Arg Val Tyr Phe Val Lys Tyr Cys Pro
                165                 170                 175

Asn His Ala His Gly Tyr Cys Phe Asn Asp Arg Leu Lys Val Tyr Asn
            180                 185                 190

Leu Gly Arg Val Lys Ser Arg Lys Ala Phe Glu Lys Ile Asn Gln His
        195                 200                 205

Gln Lys Ser Glu Leu
    210

<210> SEQ ID NO 11
<211> LENGTH: 23
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 11
cgttagtgca cttggaagaa gct                                             23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accagccatt taaatccttt ca                                              22

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cctcttgaag gtacaccaa                                                  19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tagtgcatta ggaagaagct                                                 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agcaattttg aacccttc                                                   18

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
cctcttgaag gtgtgcc                                                    17
```

CANINE CORONAVIRUS VACCINE

CROSS-REFERENCED TO RELATED APPLICATIONS

This application is a National Stage entry of International Application PCT/EP2012/062347 filed Jun. 26, 2012, which claims priority to Italian Application No. MI2011A001182 filed Jun. 28, 2011, the disclosure of each of these prior applications being hereby incorporated in their entirety by reference.

SEQUENCE LISTING

The instant application contains a Sequence Listing which has been submitted electronically in ASCII format and is hereby incorporated by reference in its entirety. Said ASCII copy, created on Mar. 24, 2014, is named 100506-00104_SL.txt and is 35,980 bytes in size.

FIELD OF THE INVENTION

The isolation of a novel pantropic canine coronavirus (CCoV) strain is described along with the production of a novel immunogenic composition comprising the CCoV strain. The strain is characterised at molecular and biological levels by, inter alia, sequence analysis.

BACKGROUND OF THE INVENTION

Coronaviruses are large, enveloped, single-strand RNA viruses that cause respiratory and/or enteric disease in mammals and birds (18). In dogs, three coronaviruses have been described so far. Canine coronavirus (CCoV) type I and type II are enteric viruses belonging to the antigenic group 1 (13), whereas canine respiratory coronavirus (CRCoV), first reported in UK by Erles et al. (19), is a group-2 coronavirus causing respiratory distress especially when associated to other pathogens (1, 9).

Type I and II CCoVs are widely distributed in Europe (7, 14) and are usually responsible for the appearance of mild to moderate gastroenteritis in pups, although death can occur as a consequence of simultaneous infections by both genotypes (5) or by other pathogens (3-11). Single CCoV infections are restricted generally to the gastroenteric tract, leading to the appearance of anorexia, diarrhoea and vomiting (Tennant et al., 1991).

Because of the widespread infections associated with CCoV, a need exists for vaccines capable of protecting against CCoV infections in canines.

SUMMARY OF THE INVENTION

The present invention provides an isolated pantropic canine coronavirus (CCoV) that does not express a functional accessory protein 3c. More particularly, the CCoV strain also does not express a functional accessory protein 3b. In another embodiment, the isolated CCoV strain comprises an isolated polynucleotide having at least 95% homology to SEQ ID NO: 1 or a complementary strand thereof. In another embodiment, the CCoV strain is inactivated by chemical treatment or heating. In another embodiment, the CCoV strain is attenuated. In another embodiment, the isolated CCoV comprises SEQ ID NO: 5.

The present invention further provides an isolated polynucleotide from a canine coronavirus (CCoV), wherein said isolated polynucleotide has at least 95% homology to SEQ ID NO: 1 or a complementary strand thereof. More particularly, said polynucleotide does not encode for a functional accessory protein 3c. In another embodiment, said polynucleotide does not encode for a functional accessory protein 3b. In another embodiment, the isolated polynucleotide consists of SEQ ID NO: 1 or a complementary strand thereof.

Another embodiment of the present invention provides an isolated polypeptide from a CCoV or plurality of polypeptides encoded by a polynucleotide having at least 95% homology to SEQ ID NO: 1. More particularly, the polynucleotide does not comprise the CB/05 strain polynucleotide. In another embodiment, said polypeptide has at least 95% homology to any one of SEQ ID NOs: 2-10. More particularly, said polypeptide is selected from any one of SEQ ID NOs: 4 or 5. More particular still, said polypeptide is SEQ ID NO: 5.

Another embodiment of the present invention provides an immunogenic composition comprising at least one of: (a) the polynucleotide, the polypeptide or the isolated canine coronavirus (CCoV) described herein; and a pharmaceutically acceptable excipient, diluent, carrier protein or adjuvant. In another embodiment, the immunogenic composition comprises an inactivated or attenuated form of the isolated canine coronavirus (CCoV). In another embodiment, the immunogenic composition comprises an isolated polypeptide from a CCoV or plurality of polypeptides encoded by a polynucleotide having at least 95% homology to SEQ ID NO: 1, wherein said polypeptide(s) are subunit antigens of the isolated CCoV. In another embodiment, the composition does not comprise an accessory protein 3c. In another embodiment, the composition does not comprise an accessory protein 3b.

Another embodiment of the invention provides an immunogenic composition as described above, for use in the treatment or prevention of a coronavirus infection in a dog. Another embodiment provides for use of the immunogenic composition in the preparation of a medicament for treatment or prevention of a coronavirus infection in a dog. Another embodiment provides a method of treating or preventing a coronavirus infection in a dog comprising administering the immunogenic composition in an amount effective to create an immunogenic response in the dog.

Another embodiment of the invention provides a canine coronavirus (CCoV) vaccine comprising at least one of: (a) a polynucleotide described above, (b) the polypeptide described above and/or (3) the isolated canine coronavirus (CCoV) strain described above.

These and other embodiments, features, and advantages of the invention will become apparent from the detailed description and the appended claims set forth herein below.

BRIEF DESCRIPTION OF THE FIGURE

The FIGURE illustrates the phylogenetic relationships of the novel CCoV strain described herein. At the phylogenetic level, strain 450/07 clustered with strain CB/05 in both S and M/N protein sequences, although a strict relatedness with recombinant CCoV/TGEV strains (CCoV-IIb) detected recently was also evident in the M/N sequences.

DETAILED DESCRIPTION

In 2005, a pantropic variant of CCoV (strain CB/05) was isolated from the internal organs of some dead pups (2) and the virus was classified as a hypervirulent biotype of CCoV-II, sharing with reference strains belonging to this genotype a high degree of genetic homology (9-12). Few aa changes in the S protein, including a Asp/His to Asn mutation at residue 125, and a 38-nt deletion in ORF3b were suggested as potential markers for the high pathogenicity of strain CB/05 (9-12). The virus isolate was demonstrated to full-fill the Koch's postulate through experimental infection of CCoV seronegative pups, that displayed severe clinical signs, including marked lymphopenia, and mortality (13). In a subsequent experiment, a striking finding was observed. In fact, seropositive dogs recovered from a recent infection caused by an enterotropic CCoV strain were susceptible to a subsequent experimental challenge with strain CB/05, showing mild clinical signs and lymphopenia (14). This may account for a limited cross-protection against the pantropic variant of enteric CCoV and, consequently, of currently available CCoV vaccines that are prepared with enteric strains.

In the present application, we have isolated a novel pantropic CCoV strain from the lungs of a pup that had died after systemic disease. The virus was characterised at the genetic level, displaying a close relatedness (more than 99% of aa identity) to the prototype strain CB/05 in all proteins encoded by the 3' end of the viral genome. Amino acid 125 of the S protein exhibited an Asn residue exactly as strain CB/05 and the 38-nt deletion in ORF3b was also confirmed, but the novel strain displayed an additional 164-deletion in ORF3c that likely prevented synthesis of the encoded accessory protein. Coronavirus accessory protein genes are believed to be dispensable for replication in vitro, but they are strictly maintained during infection of the natural hosts (26). In both pantropic CCoV strains, accessory protein 3b was truncated (22 instead of 71 aa encoded by the same gene of other CCoVs) and in the most recent one (450/07) the ORF3c product was unlikely synthesised due to the presence of an early stop codon in the 5' end of the gene. Similar deletions in the accessory protein genes of feline coronavirus have been suggested to play a certain role in the enhanced virulence showed by its hypervirulent biotype feline infectious peritonitis virus (21). The close genetic relatedness observed between strains CB/05 and 450/07 is consistent with the hypothesis that the novel strain is a direct descendant of the prototype virus. Enterotropic CCoV-II strains genetically related to CB/05 have been detected in recent years, but none of them displayed deletions in accessory protein genes (9-12). Thus, strain 450/07 may have been originated from the prototype virus through an additional 164-nt deletion in ORF3c.

At the biological level, isolates CB/05 and 450/07 were both able to infect pups and spread to their internal organs, causing systemic disease and lymphopenia. However, despite their close genetic relatedness, the two viruses showed different degrees of pathogenicity. Under experimental conditions, the prototype virus caused a severe form of disease, with the death of two out five infected pups, whereas the novel strain induced only mild to moderate clinical signs in the majority of the challenged pups. Importantly, lymphopenia was more marked in pups infected with strain CB/05 (reaching lymphocytes counts below 60% of the baseline values in all animals) than in those challenged with the novel pantropic strain that displayed an evident reduction of lymphocyte numbers only in few pups. In addition, compared to strain CB/05, the post-mortem findings induced by the novel virus were less severe and even the viral RNA titres in the faeces and internal organs were lower. This behavior may suggest a lower pathogenic potential for dogs of strain 450/07 with respect to the prototype pantropic isolate. The isolation of a new pantropic CCoV strain from a dead pup is noteworthy from an epidemiological point of view as it seems to suggest that this variant is circulating in dogs. The pantropism and lymphopenic attitude of strain CB/05 have been demonstrated (albeit at a less extent) also for the new isolate 450/07 and this biological behavior has been tentatively associated to few unique genetic changes (presence of Asn at residue 125 of the spike protein). The circulation of a CCoV cluster with pantropic and lymphopenic attitude stresses the need to develop homologous vaccines on the basis of the poor cross-protection induced by enteric CCoV (14).

Thus one embodiment of the instant invention provides a vaccine or immunogenic composition comprising a CCoV strain that does not express a functional accessory protein 3c. Another embodiment provides an isolated canine coronavirus (CCoV) that does not express a functional accessory protein 3c. More particularly, the isolated CCoV comprises a polynucleotide having at least 95% homology to SEQ ID NO: 1 or a complementary strand thereof. In another embodiment, the isolated CCoV comprises a polypeptide having SEQ ID NO: 5. In another embodiment, the isolated CCoV comprises a polypeptide having SEQ ID NO: 4. In another embodiment, the isolated CCoV comprises a polypeptide having any one of SEQ ID NOs: 2 or 6-10. In another embodiment, the isolated CCoV is inactivated by chemical treatment or heating, attenuated or is in purified subunit form.

Another embodiment of the present invention provides an isolated polynucleotide from a canine coronavirus (CCoV), wherein said isolated polynucleotide has at least 95% homology to SEQ ID NO: 1 or a complementary strand thereof. In another embodiment, said polynucleotide does not encode for a functional accessory protein 3c. In another embodiment, said polynucleotide does not encode for a functional accessory protein 3b.

In another embodiment, said polynucleotide consists of SEQ ID NO: 1 or a complementary strand thereof.

Another embodiment of the present invention provides a composition comprising an isolated polypeptide of SEQ ID NO: 5.

Another embodiment provides immunogenic composition comprising at least one of: (a) the isolated canine coronavirus (CCoV); (b) the isolated polynucleotide; and/or (c) the polypeptide as described herein; and a pharmaceutically acceptable excipient, diluent, carrier protein or adjuvant.

In another embodiment, the immunogenic composition is for use in the treatment or prevention of a coronavirus infection in a dog. Another embodiment provides for use of the immunogenic composition in the preparation of a medicament for treatment or prevention of a coronavirus infection in a dog. Another embodiment provides a method of treating or preventing a coronavirus infection in a dog comprising administering the immunogenic composition in an amount effective to create an immunogenic response in the dog.

Finally, another embodiment provides a canine coronavirus (CCoV) vaccine comprising (a) the isolated canine coronavirus (CCoV); (b) the isolated polynucleotide; and/or (c) the polypeptide as described herein.

Acronyms And Definitions

The following acronyms and definitions are used throughout the application, unless indicated otherwise. In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies, and reference to "the dosage" includes reference to one or more dosages and equivalents thereof known to those skilled in the art, and so forth.

ACRONYMS aa amino acid

CaHV canid herpesvirus

CCoV canine coronavirus
CDV canine distemper virus
CPE cytopathic effect
CPV canine parvovirus
CRM$_{197}$ diphtheria toxoid cross-reactive material 197 (gly52glu)
D-MEM Dulbecco's minimal essential medium
EDTA ethylenediaminetetraacetate
FCA Freund's complete adjuvant
IFA incomplete Freund's adjuvant
h hour
i.m. intramuscular
IF immunofluorescence
i.p. intraperitoneal
i.v. intravenous
IgG immunoglobulin G
ISCOM immunostimulating complexes
KLH Hemocyanin from *Megathura crenulata* ("keyhole limpet")
KMUA N-k-maleimidoundecanoic acid
KMUS (N-[k-maleimidoundecanoyloxy]sulfosuccinimide ester)
L liquid
LPS lipopolysaccharide
LT heat labile toxin
MDP muramyl dipeptide, also known as N-acetyl-muramyl-L-alanyl-D-isoglutamine
min minutes
NO not observed
orf open reading frame
p.o. orally
PBS phosphate buffered saline
PBST PBS with Tween 20
Poly rA:Poly rU poly-adenylic acid-poly-uridylic acid complex
POP-POE polyoxypropylenepolyoxyethylene
PT pertussis toxin
RAS Ribi™ adjuvant system
RPM revolutions per minute
s.c. subcutaneous
TCID50 median tissue culture infective dose
TGEV transmissible gastroenteritis coronavirus (Purdue Strain)
TNF tumor necrosis factor
WBC white blood cells
wk week
wt weight
Definitions Unless defined otherwise, all technical and scientific terms used herein have the same meaning as commonly understood by one of ordinary skill in the art. The following terms are provided below.

An "immunogenic composition" is a preparation containing an immunogen, including, e.g., a protein, a peptide, a whole cell, inactivated, subunit or attenuated virus, or a polysaccharide, or combination thereof, administered to stimulate the recipient's humoral and cellular immune systems to one or more of the antigens present in the immunogenic composition. "Immunization" is the process of administering an immunogenic composition and stimulating an immune or immunogenic response to an antigen in a host. Preferred hosts are mammals, such as dogs.

An "immune response" refers to the activities of the immune system, including activation and proliferation of specific cytotoxic T-cells and B-cells resulting in antigen-specific antibody production, after contact with an antigen.

An "antigen" is any agent, e.g., a protein (or immunogenic fragments of proteins such as a fragment of an adhesion protein), a peptide or peptide conjugate, immunogen, or a polysaccharide, that elicits an immune response. In this instance, the antigen preferably comprises a coronavirus antigen. The immunogenic composition can comprise one or more coronavirus antigens or immunogens.

A "unit dose" is a defined and predetermined concentration or amount of the immunogenic composition that is safe and effective to elicit an immune response in the recipient of the composition.

The term "subunit" refers to a a suspension of antigenic materials that is separated from the virulent host organism.

The term "therapeutic" as used herein means a treatment and/or prophylaxis. A therapeutic effect is obtained by suppression, remission, prevention or eradication of a disease state caused by CCoV.

The term "effective amount" as used herein means an amount that is determined by such considerations as are known in the art for vaccination and/or treating coronavirus infections (e.g., CCoV infections), wherein it is effective to provide measurable relief in treated subjects, such as exhibiting improvements including, but not limited to, improved survival rate, more rapid recovery, improvement or elimination of symptoms, reduction of post infectious complications and, where appropriate, antibody titer or increased titer against the infectious agent, and other measurements as known to those skilled in the art (e.g., measured via a blood sample).

The term "isolated" refers to a substance that is either in substantially pure form, for example, greater than about 95% purity; or purified in some way from its natural environment. An "isolated" strain (e.g. CCoV) indicates a strain that is removed from its natural environment, such as from a host animal/dog, and/or in a growth media. The term "isolated" encompasses immunogens or CCoV strains that are in solution with other agents/diluents/excipients/adjuvants.

"Parenteral" administration of an immunogenic composition includes, e.g., subcutaneous (s.c.), intravenous (i.v.), intramuscular (i.m.), or intrasternal injection or infusion techniques.

"Pharmaceutically acceptable" means a material that is not biologically or otherwise undesirable, i.e., the material can be administered to a subject without causing unacceptable biological effects (i.e. death) or interacting in a deleterious manner with any of the other components of the composition in which it is contained.

By "adjuvant" is meant a substance that serves to enhance the immunogenicity of an immunogenic composition. Thus, adjuvants are often given to boost the immune response and are well known in the art. Desirable characteristics of adjuvants include: (1) lack of toxicity; (2) ability to stimulate a long-lasting immune response; (3) simplicity of manufacture and stability in long-term storage; (4) ability to elicit both cell-mediated immunity (CMI) and humoral immune response (HIR) to antigens administered by various routes, if required; (5) synergy with other adjuvants; (6) capability of selectively interacting with populations of antigen presenting cells; (7) ability to specifically elicit appropriate Th1 or Th2 cell-specific immune responses; and (8) ability to selectively increase appropriate antibody isotype levels (e.g., IgA) against antigens.

Thus, the immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms); the interferons-α, -β and -γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (International PCT Publication No. WO 90/14837) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% Tween 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed Bordetella; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); Mycobacterium tuberculosis; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., International PCT Publication Nos. WO 00/18434, WO 02/098368 and WO 02/098369); or an E. coli heat-labile toxin (LT), particularly LT-K63, LT-R72, PT-K9/G129; see, e.g., International PCT Publication Nos. WO 93/13302 and WO 92/19265.

Exemplary conventional carrier proteins can also be used with the immunogenic compositions/antigens/CCoV strains described herein. Carrier proteins are preferably proteins that are non-toxic and non-reactogenic and obtainable in sufficient amount and purity. Carrier proteins should be amenable to standard conjugation procedures. In a particular embodiment, $CRM_{197}$ is used as the carrier protein. In other embodiments, a carrier protein of the invention is an enzymatically inactive streptococcal C5a peptidase (SCP) (e.g., one or more of the SCP variants described in U.S. Pat. Nos. 6,270,775; 6,355,255; and 6,951,653). Other suitable carrier proteins include inactivated bacterial toxins such as tetanus toxoid, pertussis toxoid, cholera toxoid (e.g., CT E29H, described in International PCT Publication No. WO2004/083251), E. coli LT, E. coli ST, E. coli DnaK protein, and exotoxin A from Pseudomonas aeruginosa. Bacterial outer membrane proteins such as outer membrane complex c (OMPC), porins, transferrin binding proteins, pneumolysin toxin (e.g., U.S. Pat. No. 5,565,204), pneumolysin toxoid (e.g., International PCT Publication No. WO 2005/108580) pneumococcal surface protein A (PspA), pneumococcal adhesin protein (PsaA), or Haemophilus influenzae protein D, can also be used. Bacterial heat shock proteins, such as mycobacterial hsp-70 can also be used. Other proteins, such as Staphylococcus epidermidis proteins SdrG, SitC and ferrochrome binding proteins, and Staphylococcus aureus proteins ClfA, ClfB and FnbA can also be used. Still other proteins, such as ovalbumin, keyhole limpet hemocyanin (KLH), glutathione S-transferase (GST), bovine serum albumin (BSA), galactokinase (galK), ubiquitin, β-galactosidase, influenza NS1 protein, or purified protein derivative of tuberculin (PPD) can also be used as carrier proteins. Virus-like particles, for example from rotavirus VP6 or from bacteriophage Qβ, can also be used.

One of skill in the art can readily select an appropriate carrier for use in this context. Methods for coupling compounds to carrier proteins are known in the art. See, e.g., ED HARLOW AND DAVID LANE, ANTIBODIES: A LABORATORY MANUAL (1988); and GREG T. HERMANSON, BIOCONJUGATE TECHNIQUES (Academic Press 1996).

The compositions disclosed can be administered in a variety of ways. It should be noted that the pharmaceutical composition containing the immunogen(s) can be administered alone or in combination with one or more pharmaceutically acceptable carriers, stabilizers, preservatives, colorants, flavorants, and excipients.

The CCoV and related compositions disclosed can be formulated with conventional carriers and excipients, which are selected in accord with ordinary practice. Aqueous formulations are prepared in sterile form, and when intended for delivery by routes other than oral administration, generally are isotonic. All formulations optionally contain excipients such as those provided for example in the HANDBOOK OF PHARMACEUTICAL EXCIPIENTS (5th ed., Raymond C. Rowe et al., eds., 2006). Excipients include ascorbic acid and other antioxidants, chelating agents (e.g., EGTA and EDTA), carbohydrates (e.g., dextrin), hydroxyalkylcellulose, hydroxyalkylmethylcellulose, stearic acid, and the like. The pH of the formulations ranges from about 3 to about 11, but is ordinarily about 7 to about 10.

Examples of physiologically acceptable carriers for routes of administration other than oral administration include but are not limited to saline solutions (e.g., normal saline, Ringer's solution, PBS (phosphate-buffered saline); polysorbate 80; L-arginine; polyvinylpyrrolidone; α-D-glucopyranosyl; α-D-glucopyranoside (trehalose); and combinations, thereof. For example, trehalose can be present in the composition in an amount from about 2 to about 10% weight/volume of the composition. In another example, when trehalose and polysorbate 80 are both present in the composition, trehalose can be present in the amount of about 4 to about 6% wt./vol. and the polysorbate 80 can be present in the amount of about 0.001 to 0.01% (wt./vol.) and generally mixtures of various physiologically compatible salts including potassium and phosphate salts with or without sugar additives (e.g., glucose).

Suitable excipients for use in the immunogenic formulations are, for example, water, saline, dextrose, glycerol, and ethanol. Non-toxic auxiliary substances, such as wetting agents, buffers, stabilizers, or emulsifiers can also be added to the composition.

Parenteral administration, if used, is generally characterized by injection. Sterile injectables can be prepared in conventional forms, either as liquid solutions or suspensions, solid forms suitable for solution or suspension in liquid prior to injection, or as emulsions.

Methods of Treatment and Administration

For each recipient, the total amount of the composition necessary for administration can be derived from protocols for immunization. The exact amount of such immunogenic compositions required may vary from dog to dog, depending on the breed, age, weight, and general condition of the dog, its mode of administration, whether it is administered with another antigen, adjuvant and the like. Generally, dosage will approximate that which is typical for the administration of other immunogenic compositions.

The immunogenic composition is typically administered as a sterile composition. The immunogenic composition can be administered by any suitable means, e.g., parenteral (including subcutaneous, intramuscular, intravenous, intradermal, perilymphatic, intranasal, intrapleuric, intrapulmonary, intrathecal, and epidural) or orally. Other routes include rectal, nasal, intranasal, topical (including buccal and sublingual), and vaginal. It is appreciated that the preferred route can vary with, for example, the condition of the recipient. An appropriate evaluation of the time and method for delivery of immunogenic compositions is well within the skill of the clinician/veterinarian. For example, the first dose can be administered at the elected date and a second dose can follow several weeks to several months from the first dose. Additional booster doses of the original immunogenic composition or modified forms can be administered as necessary (e.g., annually).

While it is possible for the active ingredients to be administered alone, it can be preferable to present them as immunogenic formulations. The formulations may include at least one active ingredient together with an acceptable carrier, excipients, adjuvants and/or, optionally, other non-active and/or active ingredients.

The formulations include those suitable for the foregoing administration routes. The formulations can conveniently be presented in unit dosage form and can be prepared by any of the methods well known in the art of pharmacy. Techniques and formulations generally are found in REMINGTON'S PHARMACEUTICAL SCIENCES (Mack Publishing Co., Easton, Pa.). Such methods include the step of bringing into association the active ingredient with the carrier, which constitutes one or more accessory ingredients. In general, the formulations are prepared by uniformly and intimately bringing into association the active ingredient with liquid carriers or finely divided solid carriers or both, and then, if necessary, shaping the product.

The oil phase of the emulsions of this invention can be constituted from known ingredients in a known manner. While the phase can comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat.

Emulients and emulsion stabilizers suitable for use in the formulation of the invention include but are not limited to Tween® 60 (as well as other polyoxyethylene sorbitan ester surfactants), Span® 80, cetostearyl alcohol, benzyl alcohol, myristyl alcohol, glyceryl mono-stearate, and sodium lauryl sulfate.

Formulations suitable for nasal administration have a particle size, for example, in the range of 0.1 to 500 microns (including particle sizes in a range between 0.1 and 500 microns in incremental microns such as 0.5, 1, 30, 35, etc.), which is administered by rapid inhalation through the nasal passage. Suitable formulations include aqueous or oily solutions of the active ingredient. Squalene is an exemplary carrier.

Formulations suitable for parenteral administration include aqueous and nonaqueous, isotonic, sterile injection solutions that can contain antioxidants, buffers, bacteriostats, and solutes, which render the formulation isotonic with the blood of the intended recipient, and aqueous and nonaqueous sterile suspensions that can include suspending agents and thickening agents.

The formulations are presented in unit-dose or multi-dose containers, for example, sealed ampules and vials, and can be stored in a freeze-dried (lyophilized) condition requiring only the addition of the sterile liquid carrier, for example, water for injection, immediately prior to use. Injection solutions and suspensions are prepared from sterile powders, and granules of the kind previously described.

Veterinary carriers are materials useful for the purpose of administering the composition and can be solid, liquid or gaseous materials, which are otherwise inert or acceptable in the veterinary art and are compatible with the active ingredient. These veterinary compositions can be administered orally, parenterally, or by any other desired route.

A formulation of the present invention can be administered to the patient-dog in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet, which slowly dissolves after being implanted, or a biocompatible delivery module well known to those skilled in the art. Such well-known dosage forms and modules are designed such that the active ingredients are slowly released over a period of several days to several weeks.

The compounds and compositions can also be used in combination with other active ingredients. Such combinations are selected based on the condition to be treated, cross-reactivities of ingredients, and pharmacological properties of the combination. Additionally, the compositions and compounds described herein can also be administered in conjunction with other conventional agents used to treat viral infections, such as antivirals, antipyretics, immunogens and analgesics. These compounds and compositions can be administered together with, or in the same course of, therapy with the compounds and compositions described herein. The individual components of the combination can be administered either sequentially or simultaneously in separate or combined pharmaceutical formulations.

Passive Immunity Therapies

Another aspect provided herein are methods and compositions for treating a subject to induce passive immunity. Compositions comprising an immunotherapeutic agent against nosocomial infections can be prepared and administered to the subject animal. The plasma from the immunized animal is then collected, and a hyperimmune globulin harvested from the plasma that contains anti-CCoV and, if included, other anti-carrier protein antibodies. The hyperimmune globulin can be used for inducing passive immunity to coronavirus infections.

The immunogenic compositions are administered to a subject-dog to induce a humoral immune response. The recipient then acts as a source of immunoglobulin (i.e., hyperimmune immunoglobulin) that is produced in response to the immunogenic composition. The immunized subject-dog donates plasma, from which the hyperimmune globulin is then obtained via, for example, conventional plasma fractionation technology. The fraction comprising anti-CCoV antibodies can then be administered to another subject-dog in order to impart resistance against or to treat a canine coronavirus infection.

For a more clear understanding, and in order to illustrate the invention more clearly, specific examples thereof are set forth hereinbelow. The following examples are merely illustrative and are not to be understood as limiting the scope and underlying principles of the invention in any way.

EXAMPLES

A. Clinical Case

A 60-day-old miniature pinscher died after displaying systemic disease characterised by fever (39.5-40° C.), leucopenia ($4.7\times10^9$ cells/l, reference range 6-17$\times10^9$ cells/l), mainly lymphopenia ($0.5\times10^9$ cells/l, reference range 1.0-4.8$\times10^9$ cells/l), lethargy, anorexia, vomiting and haemorrhagic diarrhoea. The puppy had been administered, ten days before death, a single dose of a vaccine containing canine parvovirus, canine distemper virus, canine adenovirus type 2, *Leptospira canicola* and *Leptospira icterohaemorrhagie*. A supportive therapy with antibiotics (amoxicillin/clavulanic acid) and fluids (lactated Ringer's solution) did not succeed in any improvement of the clinical conditions that continued to deteriorate until the pup's death.

Necropsy revealed gross lesions in the alimentary tract (haemorrhagic enteritis), tonsils (necrotic areas), lungs (fibrinous pneumonia), liver (enlargement and areas of necrosis), spleen (enlargement) and kidneys (degeneration of the cortex). During post-mortem examination, samples were collected from brain, lungs, spleen, liver, mesenteric lymph nodes, kidneys, and intestinal content.

B. RNA/DNA Extraction

For RNA purification, the tissue samples were homogenised (50% w/v) in Dulbecco's minimal essential medium (D-MEM) using a Tissue lyser (QIAGEN S.p.A., Milan Italy), whereas the intestinal content was homogenised (10% wt/vol) in D-MEM by vortexing. After a brief centrifugation at 8,000×g for 3 min, 140 μl of the supernatants were submitted to RNA extraction using the QIAamp® Viral RNA Mini Kit (QIAGEN S.p.A.). DNA was extracted from the tissue samples and intestinal content by DNeasy Tissue Kit and QIAamp Viral RNA Mini Kit (QIAGEN S.p.A., Milan, Italy).

C. Virological Investigations

Intestinal contents and tissue samples collected from the dead dog were tested for molecular detection of the main viral pathogens of dogs, such as CCoV (4, 5), reoviruses (Leary et al., 2002), rotaviruses (20), caliciviruses (24), canine parvovirus type 2 (CPV-2) (7, 8), canine adenoviruses type 1 and type 2 (23), canine distemper virus (CDV) (17), canid herpesvirus type 1 (CaHV-1) (31).

D. Real-time RT-PCR Assays for CCoV Characterisation

Characterization of the CCoV genotypes was carried out by means of type-specific real-time RT-PCR assays (5, 6). Reverse transcriptions and real-time PCR amplifications were performed as for CCoV detection, but with different sets of primers/probes: primer pair CCoVI-F (CGTTAGTGCACTTGGAAGAAGCT)/CCoVI-R (SEQ ID NO:11) (ACCAGCCATTTTAAATCCTTCA) (SEQ ID NO:12) and probe CCoVI-Pb (FAM-CCTCTTGAAGGTACACCAA-TAMRA) (SEQ ID NO:13) were used for CCoV type I detection, whereas primer pair CCoVII-F (TAGTGCATTAGGAAGAAGCT)/CCoVII-R (SEQ ID NO:14) (AGCAATTTTGAACCCTTC) (SEQ ID NO:15) and probe CCoVII-Pb (FAM-CCTCTTGAAGGTGTGCC-TAMRA) (SEQ ID NO:16) were employed for CCoV-II detection. The thermal profile consisted of activation of iTaq DNA polymerase at 95° C. for 10 min, followed by 45 cycles of denaturation at 95° C. for 15 s, annealing at 53° C. (CCoV type I-specific assay) or 48° C. (CCoV type II-specific assay) for 30 s and extension at 60° C. for 1 min.

E. Amplification and Sequence Analysis of the Genomic 3' End from the CCoV-positive Lung Sample The 3' end of the genome of the pantropic CCoV strain detected in the lungs was amplified using SuperScript™ One-Step RT-PCR for Long Templates (Life Technologies, Invitrogen srl, Milan, Italy), as previously described (9, 10, 11). Seven partially overlapping fragments were amplified that encompass ORFs 2 (S gene), 3a, 3b, 3c, 4 (E gene), 5 (M gene), 6 (N gene), 7a and 7b. The PCR-amplified products were sequenced by Genome Express (Meylan, France) and the obtained sequences were assembled and analyzed using the BioEdit software package (22) and the NCBI's (http://www.ncbi.nlm.nih.gov) and EMBL's (http://www.ebi.ac.uk) analysis tools. Nucleotide sequences obtained in this study were deposited in the GenBank database (http://www.ncbi.nlm.nih.gov) under accession number GU146061. The nucleotide (nt) sequences of the different ORFs were converted into amino acid (aa) sequences, that were used for comparative analysis with the prototype pantropic CCoV strain CB/05 (GenBank accession number DQ112226) and reference coronavirus strains. Phylogenetic and molecular evolutionary analyses were conducted using Mega3 (25). Phylogenetic trees, based on the S and M-N proteins of strain 450/07 were elaborated using both parsimony and neighbor-joining methods, supplying a statistical support with bootstrapping over 1000 replicates.

F. Virus Isolation

The lung of the dead pup was homogenised (10% w/v) in D-MEM together with antibiotics (penicillin 5000 IU/ml, streptomycin 2500 μg/ml, amphotericin B 10 μg/ml), and inoculated into canine fibroma (A-72) cells. Infected cells were monitored daily for the occurrence of cytopathic effect (CPE) and, after 5 days of incubation, they were tested for CCoV antigen by an immunofluorescence (IF) assay using a monoclonal antibody targeting the N protein (courtesy of Dr. Gill Chappuis, Merial, France).

G. Experimental Infection of Dogs Nine 10-11-week-old antibody-profile defined beagles from the same litter were used for this challenge study after an acclimatization period of seven days. The study was conducted at the isolation unit of the Animal Hospital, Faculty of Veterinary Medicine of Bari (Italy) according to the animal health and well-being regulations and was authorized by the Italian Ministry of Health (authorization no. 57/2006-C). All animals were seronegative to CCoV by ELISA and by PCR test from rectal swabs collected before study start (day −10 and day −1). Dogs were also negative to a CPV shedding PCR test from rectal swabs, but had been vaccinated in the kennel against CPV and tested positive to CPV serum antibodies. Dogs were housed in individual cages in three separate rooms at their arrival for acclimation and then re-allocated on day −3 through randomization in two different groups (T01 and T02, Table 1).

TABLE 1

Study design: treatment groups and challenge material

| Treatment Group | Number of animals | Animal ID | Challenge Material |
|---|---|---|---|
| T01 | 3 | 9315<br>9317<br>9321 | Cryolysate of A-72 cells |
| T02 | 6 | 9316<br>9318<br>9320<br>9314<br>9319<br>9322 | CCoV 450/07 ($3^{rd}$ passage on A-72 cells) |

Each dog was individually housed for the administration of the challenge and to monitor clinical signs. All animals were weighed on study day −3, −1, 3, and 5. On study day 0, the 6 dogs in treatment group T02 were challenged with a total volume of 4 mL (3.0 mL orally and 1.0 mL intra-nasally; 0.5 mL per nostril) containing $10^5$ TCID$_{50}$/mL of strain 450/07 ($3^{rd}$ passage on A-72 cells). Three control dogs in group T01 received the same volume of a cryolysate of uninfected A-72 cells by the same route of administration. All dogs were monitored daily for clinical signs by the attending veterinarian starting on day −1 (before challenge) and for as long as the animals remained in the study. The general health of each animal was assessed using the scoring system described in Table 2. Scores were used to assess the general health of individual animals and their treatment groups.

TABLE 2

Scoring system for general health observations during the challenge trial

| Parameter | Result | Score |
|---|---|---|
| General appearance | Normal | 0 |
| | Depressed/Lethargic | 2 |
| | Difficulties in breathing | 3 |
| | Death | 20 |
| Dehydration | None (<4%): not detectable | 0 |
| | Mild (4-5%): subtle loss of skin elasticity | 1 |
| | Moderate (6-8%): definite delay in return of skin to normal position; eyes possibly sunken in orbits; slightly prolonged capillary refill time; possibly dry mucous membranes | 2 |
| | Severe (10-15%): tented skin standing in place; prolonged capillary refill time; eyes sunken in orbits; dry mucous membranes possible signs of shock (increased heart rate, weak pulses); death imminent | 3 |

TABLE 2-continued

Scoring system for general health observations during the challenge trial

| Parameter | Result | Score |
|---|---|---|
| Diarrhea | None | 0 |
| | Soft | 1 |
| | Liquid | 2 |
| | Bloody | 3 |
| Rectal temperature | 37.0-39.4° C. | 0 |
| | ≥39.5° C. | 2 |
| | ≤37.0° C. | 3 |
| Body weight | Weight loss | 2 |
| | No weight loss | 1 |
| | Weight gain | 0 |

Blood samples were collected from each dog. EDTA-blood and serum samples were collected from the jugular vein on study days −3, 0 (pre-challenge), 3, and 5 (day of necropsy) for complete and differential blood cell counts and detection of CCoV antibodies, respectively. Rectal temperatures (° C.) were measured at arrival, on study day −3, and then daily until study day 5. Nasal and rectal swabs were collected on study days −3, −1, 3, and 5.

Five days post-challenge, all dogs were sedated by intravenous administration of 10 mg/kg of body weight of Zoletil® 100 (Virbac S.r.l., Italy) and euthanized by intravenous administration of 0.5 mL/kg of body weight of Tanax® (Intervet Italia, Italy). During necropsy, samples for virus isolation and real-time RT-PCR were collected from small intestine, mesenteric, intermandibular and popliteal lymph nodes, lung, liver, spleen, and kidney. Fresh tissue samples were collected in D-MEM and RNA Later Solution (QIAGEN S.p.A.) for viral isolation and real-time RT-PCR assays, respectively, and kept at −70° C. until used.

EDTA-blood samples and faecal swabs collected intra-vitam, as well as tissue samples collected at necropsy examination, were tested for CCoV by virus isolation on A-72 cells (9, 13) and/or by real-time RT-PCR (3, 4). CCoV antibodies were searched for in the serum samples by ELISA and virus-neutralisation tests, as previously described (29; 13).

Results

H. Identification of a CB/05-Like Strain in Internal Organs of the Dead Dog

The intestinal content and tissue samples of the dead dog (450/07) tested negative for all viral pathogens with the exception of CCoV. By real-time RT-PCR (Decaro et al., 2004), the highest viral RNA load ($5.81 \times 10^6$ RNA copies/µL of template) was found in the lung sample, but the virus was also detected in the intestinal content ($8.57 \times 10^5$ RNA copies/µL of template), mesenteric lymph nodes ($2.31 \times 10^5$ RNA copies/µL of template), spleen ($1.78 \times 10^4$ RNA copies/µL of template), liver ($3.43 \times 10^3$ RNA copies/µL of template), kidney ($7.09 \times 10^3$ RNA copies/µL of template). Only traces of CCoV RNA ($4.36 \times 10^1$ RNA copies/µL of template) were detected in the brain sample. The virus (strain 450/07) was characterized as CCoV-II by means of the genotype-specific TaqMan assays (5, 6).

The lung sample having the highest viral was used for virus isolation attempts, that were already successful at the first passage, as confirmed by occurrence of CPE and positive staining by the IF assay. Three serial passages were carried out in order to obtain a stock virus of strain 450/07 for the challenge experiment, which had a titre of $10^5$ TCID$_{50}$/mL of viral suspension. The stock virus was tested for the presence of other viral pathogens of the dog and for sterility from aerobe and anaerobe bacteria, mycoplasmas and mycetes and no contaminant agent was detected.

The 3' end of the genome of strain 450/07 was amplified from the lung material through amplification of seven overlapping fragments. The obtained sequence was 8,618 nt long and contained the full length of ORFs 2, 3a, 3b, 3c, 4, 5, 6, 7a and 7b. The S protein (ORF2 product) was 1454-aa long exactly as that of prototype strain CB/05, to which the new pantropic isolate was highly related at this level (99.5% aa identity). A high degree of genetic relatedness was found also in the other structural proteins, including the E (82 aa, 100% identity), M (262 aa, 99.2% identity) and N (382 aa, 99.7% identity) proteins, encoded by ORFs 4, 5, and 6, respectively. Products of ORFs 3a (71 aa), 3b (22 aa), 7a (101 aa) and 7b (213 aa) were intact with respect to prototype strain CB/05. The 38-nt deletion in ORF3b found in strain CB/05 was also detected in strain 450/07, which exhibited an additional 164-nt deletion in ORF3c. This deletion was responsible for a change in the frame shift and the consequent introduction of a very early stop codon at nt 4824 of the sequenced genomic region that should prevent the synthesis of the ORF3c product.

At the phylogenetic level, strain 450/07 clustered with strain CB/05 in both S and M/N protein sequences, although a strict relatedness with recombinant CCoV/TGEV strains (CCoV-IIb) detected recently (16) was also evident in the M/N sequences (FIGURE).

I. Clinical, Post-Mortem and Virological Findings in Experimentally Infected Dogs A summary of all the clinical sings recorded daily is shown in Table 3.

group were mildly to severe dehydrated on days 3 and 4 after challenge. Soft faeces or diarrhoea were observed in four T02 dogs on days 3 and 4 after challenge. All six dogs in T02 had lymphadenomegalia on days 3, 4 or 5 in one of the dogs (9322), on days 4 and 5 on two dogs (9314 and 9319) and on day 5 in the other three dogs. Dog 9322 had also nasal secretion on days 0, 1 and 4 post challenge and dog 9314 had decreased capillar refill and pale mucosa on day 5. Based on the scoring system reported in Table 2, two of the three control pups had a clinical score of zero because they did not show any clinical signs. One of the T01 dogs lost weight on days 3 and 5 after challenge but did not show any other clinical sign. This pup had therefore a score of 4 with its group showing a mean score of 1.3. However, all six pups in T02 group showed a variety of clinical sings, which lasted between one and three days and therefore their scores ranged from 2 to 19 (mean 5.7).

Day −3 and Day 0 lymphocyte and WBC counts per μL were averaged and were used as baseline levels to compare to the day 3 post-challenge levels. Lymphocyte counts decreased ≥30% in five dogs in T02, but less than 30% in the rest of dogs in T02 and T01. WBC counts decreased ≥30% in four of six dogs in T02, but less than ≥30% the dogs left in T02 and in all the control dogs (T01) (Table 4). The reduction in the lymphocyte counts were particularly dramatic for dog 9322 (75% with respect to the baseline values), that was the one that started showing clinical signs earlier and also showed the most severe clinical signs.

TABLE 3

Summary of clinical signs observed on study days (D) in control dogs (T01) and in dogs experimentally infected with strain 450/07 (T02)

| Treat. group | Dog ID | Depression | Diarrhea[1] | Dehydration[2] | Fever | Body weight D −1 vs. D3/D5 | Enlargement of lymph nodes | Other |
|---|---|---|---|---|---|---|---|---|
| T01 | 9315 | NO | NO | NO | NO | Gain | NO | NO |
| | 9317 | NO | NO | NO | NO | Gain | NO | NO |
| | 9321 | NO | NO | NO | NO | Loss | NO | NO |
| T02 | 9316 | NO | NO | NO | NO | Loss | D5 | NO |
| | 9318 | D5 | D4(S) D5(S) | NO | NO | Loss | D5 | NO |
| | 9320 | NO | D4(S) | NO | NO | Loss | D5 | NO |
| | 9314 | NO | NO | NO | NO | Loss | D4, D5 | Decreased capillar refill and pale mucosa (D5) |
| | 9319 | NO | D5(S) | D5(M) | D4 | Loss | D4, D5 | NO |
| | 9322 | D4, D5, | D3(S), D4(L) D4(S) | D4(S) | NO | Loss | D3, D4, D5 | Nasal secretion (D1, D2, D4) |

NO, Not observed.
[1]S, soft; L, liquid.
[2]M, moderate; S, severe.

All six dogs in T02 and one of three control dogs in T01 lost weight on day 3 after challenge compared to their (baseline) weight on day −1 (before challenge). Rectal temperature in T01 and T02 dogs ranged between 37.6° C. and 38.9° C. from day −8 to day 0 before challenge. For T01 dogs, rectal temperature after challenge ranged from 37.6° C. to 38.4° C., but for T02 dogs, the range after challenge increased to be between 37.6° C. and 39.5° C. However, only one dog (9319) from T02 group had fever on day 4, but three more dogs in T02 showed a numerical increase in their rectal temperature within the normal range after challenge. This change in range was not observed in T01 control dogs. Two dogs in T02 challenged with strain 450/07 were found depressed or lethargic on days 3 and 4 after challenge and two dogs of the same

TABLE 4

Percentage reduction in lymphocyte and WBC counts on day 3 after challenge in control dogs (T01) and in dogs experimentally infected with strain 450/07 (T02)

| Treatment group | Dog ID | % Lymphocyte reduction | Group mean (%) | % WBC reduction | Group mean (%) |
|---|---|---|---|---|---|
| T01 | 9315 | 6 | 6.3 | 2 | 12 |
| | 9317 | 2 | | 0 | |
| | 9321 | 11 | | 22 | |
| T02 | 9316 | 40 | 48.6 | 20 | 33.83 |
| | 9318 | 22 | | 39 | |

TABLE 4-continued

Percentage reduction in lymphocyte and WBC counts on day 3 after challenge in control dogs (T01) and in dogs experimentally infected with strain 450/07 (T02)

| Treatment group | Dog ID | % Lymphocyte reduction | Group mean (%) | % WBC reduction | Group mean (%) |
|---|---|---|---|---|---|
| | 9320 | 54 | | 52 | |
| | 9322 | 75 | | 37 | |
| | 9319 | 47 | | 32 | |
| | 9314 | 54 | | 23 | |

At necropsy, four infected pups displayed mild to severe enteritis in one or more intestinal segments and five presented enlargement of the mesenteric lymph nodes, that were congested and with scattered haemorrhages (Table 5). Splenomegaly and involvement of popliteal and/or intermandibular lymph nodes were observed in one (9314) and two pups (9314 and 9322), respectively. Lung congestion and haemorrhages on the thymus were detected only in pup 9314, whereas in four pups abundant abdominal fluid was present. Consequently, a thymus samples and aliquots of the abdominal fluid were also collected from the lesions.

TABLE 5

Summary of post-mortem findings and virus detection in tissue samples of control dogs (T01) and of dogs experimentally infected with strain 450/07 (T02)$^a$

| Tr. grp | Dog ID | Other LN | Mesenteric LN | Liver | Lung | Spleen | Kidney | Duodenum | Jejunum | Ileum | Abdominal fluid | Thymus |
|---|---|---|---|---|---|---|---|---|---|---|---|---|
| T01 | 9315 | Neg | Neg | Neg | Neg | Neg | Neg | Neg | Neg | Neg | NC | NC |
| | 9317 | Neg | Neg | Neg | Neg | Neg | Neg | Neg | Neg | Neg | NC | NC |
| | 9321 | Neg | Neg | Neg | Neg | Neg | Neg | Neg | Neg | Neg | NC | NC |
| T02 | 9316 | Neg | $1.68 \times 10^{3\,(c)}$ | Neg | Neg | Neg | $3.93 \times 10^{1}$ | Neg | Neg | $9.02 \times 10^{0\,(c)}$ | NC | NC |
| | 9318 | Neg | Neg | Neg | Neg | Neg | Neg | Neg | Neg | Neg | Neg$^{(c)}$ | NC |
| | 9320 | Neg | $9.08 \times 10^{2\,(c)}$ | Neg | Neg | Neg | Neg | Neg | Neg | Neg | Neg$^{(c)}$ | NC |
| | 9314 | $8.84 \times 10^{2}$ (P)$^{(c)}$ | $7.29 \times 10^{5\,(b,c)}$ | $2.61 \times 10^{2}$ | $7.06 \times 10^{1\,(c)}$ | $9.35 \times 10^{2\,(c)}$ | Neg | $7.41 \times 10^{5\,(b)}$ | $5.93 \times 10^{6\,(b)}$ | $2.16 \times 10^{6\,(b,c)}$ | NC | $1.22 \times 10^{2}$ |
| | 9319 | Neg | $2.80 \times 10^{6\,(b,c)}$ | $2.01 \times 10^{1}$ | Neg | $6.11 \times 10^{1}$ | $2.92 \times 10^{2}$ | $1.79 \times 10^{0\,(c)}$ | $2.86 \times 10^{4\,(c)}$ | $2.00 \times 10^{5\,(b,c)}$ | $4.92 \times 10^{2\,(c)}$ | NC |
| | 9322 | $4.31 \times 10^{2}$ (P)$^{(c)}$ | $4.17 \times 10^{6\,(b,c)}$ | $6.93 \times 10^{0}$ | Neg | $1.51 \times 10^{0}$ | Neg | Neg | $2.45 \times 10^{2\,(c)}$ | $3.33 \times 10^{2\,(c)}$ | Neg$^{(c)}$ | NC |

LN, lymph node(s);
(P), popliteal;
Neg, negative;
NC, not collected.
$^a$CCoV titres are expressed as RNA copy numbers per μL of template.
$^b$Tissues that tested positive by virus isolation.
$^c$Tissues that displayed gross lesions at post-mortem examination.

By real-time RT-PCR, three T02 pups were excreting virus on days 3 and/or 5 in their faeces, with titres ranging from $2.75 \times 10^3$ to $1.07 \times 10^7$ CCoV RNA copies per μL of template, and the viral RNA was detected in only one day 5 blood sample of a pup in T02 (titre of $5.73 \times 10^1$ RNA copies per μL of template). As expected on the basis of the viral loads, CCoV was only isolated from a day 3 rectal swab from pup number 9314 in T02 group. Several tissues collected from five infected pups tested positive by real-time RT-PCR, with the highest titres being detected in the lymphoid tissues (Table 5). CCoV was isolated from mesenteric lymph nodes in three dogs, from duodenum and jejunum in one dog and from Ileum in two dogs from T02. Neither nasal swabs from T02 dogs nor any samples from T01 dogs tested positive to CCoV by real-time RT-PCR or virus isolation.

By both ELISA and VN tests, seroconversion against CCoV was not detected in any control or challenged dogs.

The following references, discussed in relevant part supra, are hereby incorporated by reference as if set forth fully herein.

REFERENCES (1) Buonavoglia, C. & Martella, V. (2007). Canine respiratory viruses. *Vet Res* 38, 355-373.
(2) Buonavoglia, C., Decaro, N., Martella, V., Elia, G., Campolo, M., Desario, C., Castagnaro, M., & Tempesta, M. (2006). Canine coronavirus highly pathogenic for dogs. *Emerg Infect Dis* 12, 492-494.
(3) Decaro N., Camero M., Greco G., Zizzo N., Tinelli A., Campolo M., Pratelli A. & Buonavoglia C. (2004a). Canine distemper and related diseases: report of a severe outbreak in a kennel. *New Microbiol* 27, 177-182.
(4) Decaro, N., Pratelli, A., Campolo, M., Elia, G., Martella, V., Tempesta, M. & Buonavoglia, C. (2004b). Quantitation of canine coronavirus RNA in the faeces of dogs by TaqMan RT-PCR. *J Virol Methods* 119, 145-150.
(5) Decaro, N., Elia, G., Martella, V., Desario, C., Campolo, M., Di Trani, L., Tarsitano, E., Tempesta, M. & Buonavoglia, C. (2005a). A real-time PCR assay for rapid detection and quantitation of canine parvovirus type 2 DNA in the feces of dogs. *Vet Microbiol* 105, 19-28.
(6) Decaro, N., Martella, V., Ricci, D., Elia G, Desario C, Campolo M, Cavaliere N, Di Trani L, Tempesta M. & Buonavoglia C. (2005b). Genotype-specific fluorogenic RT-PCR assays for the detection and quantitation of canine coronavirus type I and type II RNA in faecal samples of dogs. *J Virol Methods* 130, 72-78.
(7) Decaro N., Elia G., Martella V., Campolo M., Desario C., Camero M., Cirone F., Lorusso E., Lucente M. S., Narcisi D., Scalia P. & Buonavoglia C. (2006a). Characterisation of the canine parvovirus type 2 variants using minor groove binder probe technology. *J Virol Methods* 133, 92-99.
(8) Decaro, N., Martella, V., Desario, C., Bellacicco, A. L., Camero, M., Manna, L., D' aloja, D. & Buonavoglia, C. (2006b). First detection of canine parvovirus type 2c in pups with haemorrhagic enteritis in Spain. *J Vet Med B Infect Dis Vet Public Health* 53, 468-472.

(9) Decaro, N., Campolo, M., Elia, G., Buonavoglia, D., Colaianni, M. L., Lorusso, A., Mari, V. & Buonavoglia C. (2007a). Infectious canine hepatitis: An "old" disease reemerging in Italy. *Res Vet Sci* 83, 269-273.

(10) Decaro N., Desario C., Elia G., Campolo M., Lorusso A., Mari V., Martella V. & Buonavoglia C. (2007b). Occurrence of severe gastroenteritis in pups after canine parvovirus vaccine administration: a clinical and laboratory diagnostic dilemma. *Vaccine* 25, 1161-1166.

(11) Decaro, N, Desario, C., Elia, G., Mari, V., Lucente, M. S., Cordioli, P., Colaianni, M. L., Martella, V. & Buonavoglia C. (2007c). Serological and molecular evidence that canine respiratory coronavirus is circulating in Italy. *Vet Microbiol* 121, 225-230.

(12) Decaro, N., Martella, V., Elia, G., Campolo, M., Desario, C., Cirone, F., Tempesta, M. & Buonavoglia, C. (2007d). Molecular characterisation of the virulent canine coronavirus CB/05 strain. *Virus Res* 125, 54-60.

(13) Decaro, N. & Buonavoglia, C. (2008). An update on canine coronaviruses: Viral evolution and pathobiology. *Vet Microbiol* 132, 221-234.

(14) Decaro N., Desario C., Billi M., Mari V., Elia G., Cavalli A., Martella V. & Buonavoglia C. Western European epidemiological survey for parvovirus and coronavirus infections in dogs. *Vet J* in press a.

(15) Decaro N., Elia G., Martella V., Campolo M., Mari V., Desario C., Lucente M. S., Lorusso E., Kanellos T., Gibbons R. H. & Buonavoglia C. Immunity after natural exposure to enteric canine coronavirus does not provide complete protection against infection with the new pantropic CB/05 strain. *Vaccine* in press b.

(16) Decaro N., Mari V., Elia G., Addie D. D., Camero M., Lucente M. S., Martella V. & Buonavoglia C. Recombinant canine coronaviruses in dogs, Europe. *Emerg Infect Dis* in press c.

(17) Elia, G., Decaro, N., Martella, V., Cirone, F., Lucente, M. S., Lorusso, E., Di Trani, L. & Buonavoglia, C. (2006). Detection of canine distemper virus in dogs by real-time RT-PCR. *J Virol Methods* 136, 171-176.

(18) Enjuanes, L., Brian, D., Cavanagh, D., Holmes, K., Lai, M. M. C., Laude, H., Masters, P., Rottier, P., Siddell, S., Spaan, W. J. M., Taguchi, F. & Talbot, P. (2000). Family Coronaviridae. In *Virus Taxonomy, Classification and Nomenclature of Viruses*, pp. 835-849. Edited by M. H. V. van Regenmortel, C. M. Fauquet, D. H. L. Bishop, E. B. Carstens, M. K. Estes, S. M. Lemon, J. Maniloff, M. A. Mayo, D. J. McGeoch, C. T. Pringle & R. B. Wickner. New York, USA: Academic Press.

(19) Erles, K., Toomey, C., Brooks, H. W. & Brownlie, J. (2003). Detection of a group 2 coronavirus in dogs with canine infectious respiratory disease. *Virology* 310, 216-223.

(20) Gouvea, V., Santos, N., Timenetsky & Mdo C. (1994). Identification of bovine and porcine rotavirus G types by PCR. *J Clin Microbiol* 32, 1338-1340.

(21) Haijema, B. J., Rottier, P. J. M., de Groot, R. J. (2007). Feline coronaviruses: a tale of two-faced types. pp. 183-203. In *Coronaviruses. Molecular and cellular biology*, pp. 183-203. Edited by V. Thiel. Norfolk, United Kingdom: Caister Academic Press.

(22) Hall, T. A. (1999). BioEdit: a user-friendly biological sequence alignment and analysis program for Windows 95/98/NT. *Nucl Acids Symp Ser* 41, 95-98.

(23) Hu, R. L., Huang, G., Qiu, W., Zhong, Z. H., Xia, X. Z. & Yin, Z. (2001). Detection and differentiation of CAV-1 and CAV-2 by polymerase chain reaction. *Vet Res Commun* 25, 77-84.

(24) Jiang, X., Huang, P. W., Zhong, W. M., Farkas, T., Cubitt, D. W. & Matson, D. O. (1999). Design and evaluation of a primer pair that detects both Norwalk- and Sapporo-like caliciviruses by RT-PCR. *J Virol Methods* 83, 145-154.

(25) Kumar, S., Tamura, K. & Nei, M. (2004). MEGA3: integrated software for Molecular Evolutionary Genetics Analysis and sequence alignment. *Brief Bioinform* 5, 150-163.

(26) Lorusso, A., Decaro, N., Schellen, P., Rottier, P. J., Buonavoglia, C., Haijema, B. J. & de Groot, R. J. (2008). Gain, preservation and loss of a group 1a coronavirus accessory glycoprotein. *J Virol* 82, 10312-10317.

(27) Pratelli, A., Tempesta, M., Roperto, F. P., Sagazio, P., Carmichael, L. & Buonavoglia, C. (1999). Fatal coronavirus infection in puppies following canine parvovirus 2b infection. *J Vet Diagn Invest* 11, 550-553.

(28) Pratelli, A., Martella, V., Elia, G., Tempesta, M., Guarda, F., Capucchio, M. T., Carmichael, L. E. & Buonavoglia, C. (2001). Severe enteric disease in an animal shelter associated with dual infection by canine adenovirus type 1 and canine coronavirus. *J Vet Med B Infect Dis Vet Public Health* 48, 385-392.

(29) Pratelli, A., Elia, G., Martella, V., Palmieri, A., Cirone, F., Tinelli, A., Corrente, M. & Buonavoglia, C. (2002). Prevalence of canine coronavirus antibodies by an enzyme-linked immunosorbent assay in dogs in the south of Italy. *J Virol Methods* 102, 67-71.

(30) Pratelli, A., Decaro, N., Tinelli, A., Martella, V., Elia, G., Tempesta, M., Cirone, F. & Buonavoglia, C. (2004). Two genotypes of canine coronavirus simultaneously detected in fecal samples of dogs with diarrhea. *J Clin Microbiol* 42, 1797-1799.

(31) Schulze, C. & Baumgartner, W. (1998). Nested polymerase chain reaction and in situ hybridization for diagnosis of canine herpesvirus infection in puppies. *Vet Pathol* 35, 209-217.

(32) Tennant, B. J., Gaskell, R. M., Kelly, D. F., Carter, S. D. & Gaskell, C. J. (1991). Canine coronavirus infection in the dog following oronasal inoculation. *Res Vet Sci* 51, 11-18.

The invention claimed is:

1. A method of treating or preventing a coronavirus infection in a dog comprising administering an immunogenic composition comprising an isolated canine coronavirus (CCoV) that does not synthesize accessory protein 3c in an amount effective to create an immunogenic response in the dog.

2. The method of claim 1, wherein the immunogenic composition further comprises an adjuvant.

3. The method of claim 1, wherein the CCoV is inactivated or attenuated.

4. The method of claim 1, wherein the CCoV contains a deletion in the open reading frame encoding accessory protein 3c.

* * * * *